US012390400B2

(12) United States Patent
Assad et al.

(10) Patent No.: US 12,390,400 B2
(45) Date of Patent: Aug. 19, 2025

(54) SOLID DOSAGE MEDICAMENT DISPENSER AND METHODS OF USE

(71) Applicant: VISIP, LLC, Tampa, FL (US)

(72) Inventors: Andrew Assad, Tampa, FL (US); Lucas Libraro, Chicago, IL (US); Thomas Gonnot, Chicago, IL (US); Jahir Leonardo Caro, Chicago, IL (US); Oluwadurotimi Solola, Chicago, IL (US); Lee Miller, Chicago, IL (US)

(73) Assignee: VISIP, LLC, Tampa, FL (US)

( * ) Notice: Subject to any disclaimer, the term of this patent is extended or adjusted under 35 U.S.C. 154(b) by 158 days.

(21) Appl. No.: 17/151,995

(22) Filed: Jan. 19, 2021

(65) Prior Publication Data

US 2021/0220224 A1   Jul. 22, 2021

Related U.S. Application Data

(60) Provisional application No. 62/964,257, filed on Jan. 22, 2020.

(51) Int. Cl.
| | | |
|---|---|---|
| *A61J 7/00* | (2006.01) | |
| *A45C 11/00* | (2006.01) | |
| *A61J 1/03* | (2023.01) | |
| *B65D 83/04* | (2006.01) | |
| *B65G 47/91* | (2006.01) | |

(52) U.S. Cl.
CPC ............ *A61J 7/0084* (2013.01); *A45C 11/00* (2013.01); *A61J 1/03* (2013.01); *B65D 83/0409* (2013.01); *B65G 47/912* (2013.01); *B65G 47/917* (2013.01); *A45C 2011/007* (2013.01); *A61J 2205/10* (2013.01); *A61J 2205/60* (2013.01)

(58) Field of Classification Search
CPC ............... A61J 7/0084; A61J 2205/007; A61J 2205/60; A45C 11/00; B65D 83/0409; B65G 47/912; B65G 47/917
USPC ............................................................ 221/1
See application file for complete search history.

(56) References Cited

U.S. PATENT DOCUMENTS

| | | | | |
|---|---|---|---|---|
| 5,097,982 A | * | 3/1992 | Kedem ................. | A61J 7/0084 221/133 |
| 5,292,029 A | * | 3/1994 | Pearson .............. | G07F 11/1657 221/9 |
| 5,405,048 A | * | 4/1995 | Rogers ................. | B65G 1/1373 221/17 |

(Continued)

FOREIGN PATENT DOCUMENTS

| | | | | |
|---|---|---|---|---|
| WO | WO-2021231972 A1 | * | 11/2021 | .......... B25J 15/0683 |
| WO | WO-2022221778 A1 | * | 10/2022 | ................ A61J 1/03 |

OTHER PUBLICATIONS

"MedaCube: Never miss taking a pill again", https://medacube.com/, retrieved Jan. 14, 2021.

(Continued)

*Primary Examiner* — Rakesh Kumar
(74) *Attorney, Agent, or Firm* — McDonnell Boehnen Hulbert & Berghoff LLP

(57) ABSTRACT

The present disclosure provides a solid dosage medicament dispensing system including a user interface configured to receive one or more inputs from a user, and a control system configured to perform one or more functions of the solid dosage medicament dispensing system based on the one or more inputs received from the user.

11 Claims, 16 Drawing Sheets

(56) References Cited

U.S. PATENT DOCUMENTS

| | | | | |
|---|---|---|---|---|
| 5,490,610 | A * | 2/1996 | Pearson | G07F 11/62 221/211 |
| 5,571,258 | A * | 11/1996 | Pearson | G07F 17/0092 294/64.3 |
| 6,170,230 | B1 * | 1/2001 | Chudy | B65B 5/103 53/238 |
| 6,607,094 | B2 * | 8/2003 | MacDonald | G07F 11/24 221/121 |
| 6,732,884 | B2 * | 5/2004 | Topliffe | A61J 7/0481 221/121 |
| 7,587,259 | B2 * | 9/2009 | Berg | G07F 9/026 221/124 |
| 8,360,274 | B2 * | 1/2013 | Shen | B65B 35/06 221/9 |
| 9,014,847 | B2 * | 4/2015 | Dunn | G07F 9/026 700/243 |
| 9,443,370 | B2 * | 9/2016 | Carson | G07F 17/0092 |
| 9,501,887 | B2 | 11/2016 | Berg | |
| 9,550,619 | B2 | 1/2017 | Park | |
| 10,065,788 | B2 | 9/2018 | Fagen | |
| 10,555,873 | B2 * | 2/2020 | Poirier | A61J 7/0436 |
| 10,940,094 | B2 * | 3/2021 | Albanawi | A61J 7/0427 |
| 11,020,320 | B1 * | 6/2021 | Panda | A61J 7/0481 |
| 2004/0079761 | A1 * | 4/2004 | Chirnomas | A23G 9/225 221/92 |
| 2004/0155049 | A1 * | 8/2004 | Float | G07F 17/0092 221/12 |
| 2005/0192705 | A1 * | 9/2005 | Pinney | G07F 11/62 700/217 |
| 2006/0124655 | A1 * | 6/2006 | Ratnakar | G07F 11/44 221/3 |
| 2006/0213921 | A1 * | 9/2006 | Abdulhay | G07F 17/0092 221/130 |
| 2006/0259188 | A1 | 11/2006 | Berg | |
| 2007/0093932 | A1 * | 4/2007 | Abdulhay | A61J 7/0084 700/231 |
| 2008/0272138 | A1 * | 11/2008 | Ross | G07F 11/1657 705/2 |
| 2008/0272142 | A1 * | 11/2008 | Chirnomas | G07F 11/14 221/282 |
| 2010/0256808 | A1 * | 10/2010 | Hui | G07F 17/0092 221/133 |
| 2014/0025199 | A1 * | 1/2014 | Berg | G07F 17/0092 700/232 |
| 2014/0131378 | A1 * | 5/2014 | Shih | G07F 17/0092 221/258 |
| 2016/0042151 | A1 * | 2/2016 | Akdogan | B25J 19/023 700/240 |
| 2016/0355322 | A1 | 12/2016 | Burton | |
| 2017/0132867 | A1 | 5/2017 | Berg | |
| 2017/0354574 | A1 | 12/2017 | Feng | |
| 2018/0168935 | A1 * | 6/2018 | Chen | B65B 5/103 |
| 2021/0220224 | A1 * | 7/2021 | Assad | B65G 47/912 |
| 2022/0332493 | A1 * | 10/2022 | Sunada | A61J 1/03 |
| 2022/0415468 | A1 * | 12/2022 | Schoenfeld | G16H 40/63 |

OTHER PUBLICATIONS

"Smart Medication Dispensing: Stay happy, healthy and at home!", https://liviathome.com/, retrieved Jan. 14, 2021.

"Hero: Medication, Managed"; https://herohealth.com/, retrieved Jan. 14, 2021.

"Pillohealth: Bringing Health Home", https://www.pillohealth.com, retrieved Jan. 14, 2021.

"MediPENSE: RxPense® The most intelligent, secure and automatic pill dispenser", https://medipense.com/en/, retrieved Jan. 14, 2021.

"Spencer Health Solutions: Elevate outcomes in patient engagement and clinical research", https://www.helloimspencer.com/, retrieved Jan. 14, 2021.

"Karie: Make medication the easiest part of your day", http://kariehealth.com/#home, retrieved Jan. 14, 2021.

"Philips Lifeline: Philips Medication Dispenser", https://www.lifeline.philips.com/pill-dispenser/health-mdp.html, retrieved Jan. 14, 2021.

"Lumma: Smart Pill Dispenser by LITE", https://www.kickstarter.com/projects/402921688/lumma-automated-medication-sorter-and-dispenser; https://www.epill.com/dispenser.html, retrieved Jan. 14, 2021.

"TabSafe: In-Home Medication Dispensing System", https://www.tabsafe.com/, retrieved Jan. 14, 2021.

International Search Report and Written Opinion for corresponding PCT application No. PCT/US2021/13893, dated Jun. 3, 2021.

* cited by examiner

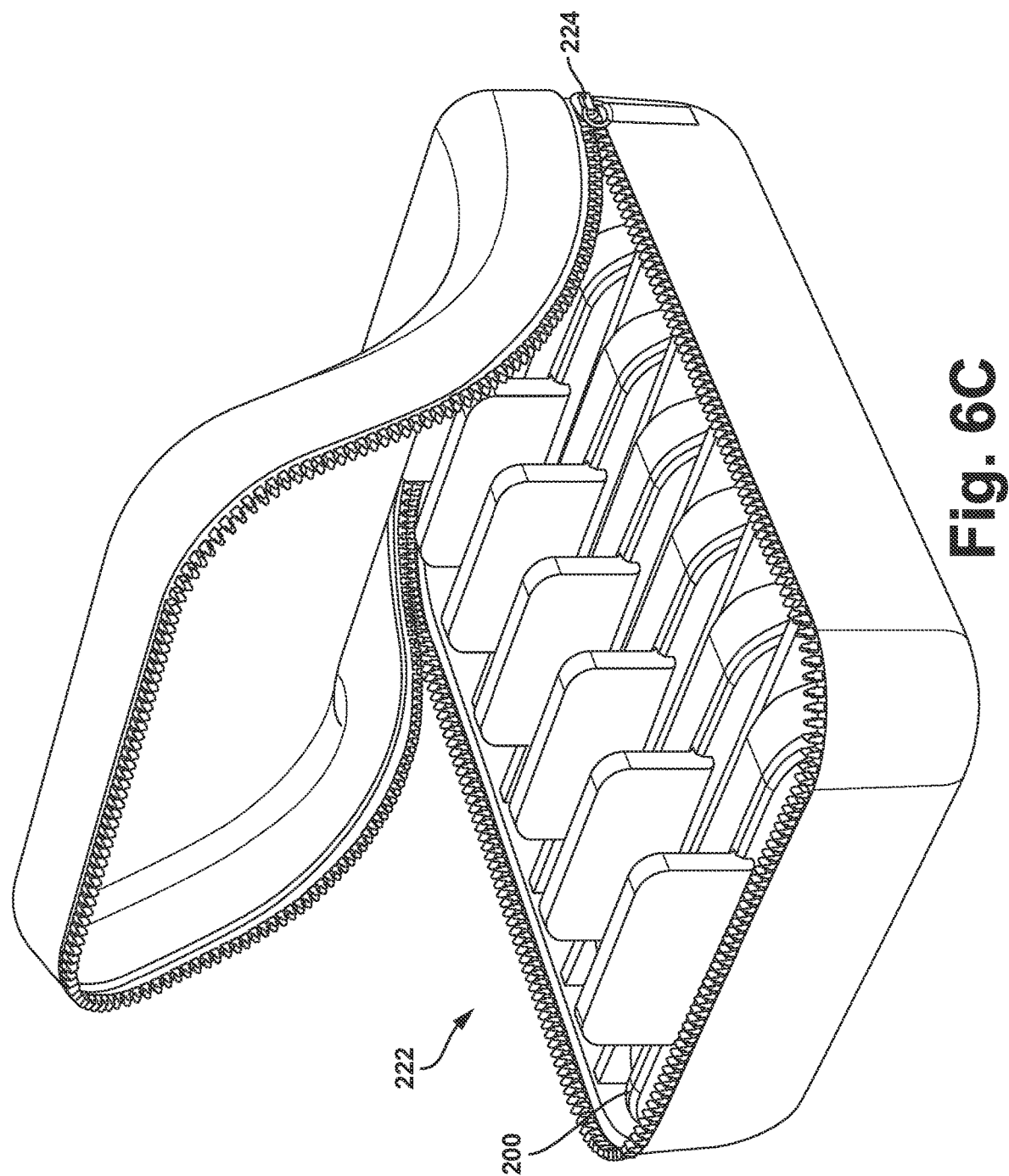

← 2 of 3

Bumetanide
500mg tablets  Qty. 30

Choose two dosage times

☑ Morning - 7:00 AM  Suggested
☐ Lunch - 12:00 PM
☐ Dinner - 6:00 PM  Suggested
☑ Bedtime - 9:00 PM

[ NEXT ]

Amoxicillan Hydrocodone
500mg tablets  Qty. 30

Choose two dosage times

☐ Morning - 7:00 AM
☑ Lunch - 12:00 PM  Suggested
☐ Dinner - 6:00 PM
☐ Bedtime - 9:00 PM

[ DONE ]

Successfully added pills

Do you have more to add?

[ ADD MORE PILLS ]

[ FINISHED ]

REVIEW MEDICATION ⊙

SOLID DOSAGE MEDICAMENT DISPENSER AND METHODS OF USE

RELATED APPLICATIONS

This application is a non-provisional of and claims priority to U.S. Provisional Application No. 62/964,257 entitled "Solid Dosage Medicament Dispenser and Methods of Use," filed on Jan. 22, 2020, which is hereby incorporated by reference in its entirety.

FIELD

The present invention relates generally to devices, systems, and methods for automated or on-demand dispensing of solid dosage medications.

BACKGROUND

Unless otherwise indicated herein, the materials described in this section are not prior art to the claims in this application and are not admitted to be prior art by inclusion in this section.

Solid dosage medications such as pills, capsules, tablets, and the like are traditionally provided in the form of a disposable plastic container having the medication name, dosage, and provider printed on the label. The current healthcare climate in which patients with chronic illnesses are required to retrieve daily doses often consisting of multiple different medications from such disposable plastic containers does not promote proper patient education, accountability, and adherence. In particular, patients that require a plurality of prescription and over-the-counter (OTC) medications frequently exhibit poor compliance in properly following the drug regimen required for each particular medication. For example, it is typical for medications to be taken in incorrect or varying dosages, on incorrect or varying days, and at incorrect or varying times. Such poor medication regimen adherence metrics can be exaggerated in geriatric patients, a group which is statistically more likely to be prescribed multiple chronic medications. While there exists a variety of products and techniques for reminding patients of their medication regimens, these known systems have had limited success as a result of cost, reliability, and/or complexity. Accordingly, an improved solid dosage medication dispenser and methods of use is needed.

SUMMARY

In one example, the present disclosure provides a solid dosage medicament dispensing system comprising (a) a housing, (b) a tray coupled to the housing, wherein the tray is configured to receive one or more containers, and wherein the tray is configured to translate from a first position within the housing to a second position in which the tray is positioned to receive the one or more containers, (c) a pre-dispending tray, (d) a retrieval probe moveable between the one or more containers and the pre-dispensing tray, (e) a user interface configured to receive one or more inputs from a user, and (f) a control system configured to perform one or more functions of the solid dosage medicament dispensing system based on the one or more inputs received from the user.

In another example, the present disclosure provides a container comprising (a) a base having an interior surface and an exterior surface, wherein the interior surface of the base has a radius of curvature greater than zero, (b) a sidewall having a first end coupled to the base and a second end opposite the first end, wherein an interior surface of the sidewall and the interior surface of the base define a chamber therebetween, and wherein the second end of the sidewall defines an opening, and (c) a removable cap removably coupled to the second end of the sidewall to thereby cover the opening.

In another example, the present disclosure provides a container comprising (a) a base having an interior surface and an exterior surface, (b) a sidewall having a first end coupled to the base and a second end opposite the first end, wherein the second end of the sidewall defines an opening, (c) a plurality of dividers each coupled to the interior surface of the base and an interior surface of the sidewall, wherein the interior surface of the sidewall, the interior surface of the base, and the plurality of dividers define a plurality of chambers therebetween, and (d) a removable cover removably coupled to the second end of the sidewall to thereby cover the opening, wherein the removable cover includes a visual indication of a time of day positioned over each of the plurality of chambers when the removable cover is positioned over the opening.

In another example, the present disclosure provides a method comprising (a) vibrating a tray including one or more containers, wherein each container of the one or more containers includes a solid dosage medicament, (b) moving a retrieval probe to a location above a container of the one or more containers, (c) lowering the retrieval probe into the container to capture a solid dosage medicament from the container, (d) determining whether the retrieval probe has captured the solid dosage medicament, (e) in response to a determination that the retrieval probe has captured the solid dosage medicament, moving the retrieval probe to a pre-dispensing tray, (f) releasing the solid dosage medicament from the retrieval probe into the pre-dispensing tray, (g) if a user input is received at a user interface, dispensing the solid dosage medicament to an exterior of the housing, and (h) if no user input is received at the user interface, (i) moving the retrieval probe to the pre-dispensing tray, (ii) capturing the solid dosage medicament from the pre-dispensing tray, and (iii) returning the solid dosage medicament to the container.

In yet another example, the present disclosure provides a method comprising (a) providing, at a user interface, a plurality of preferred times corresponding to a plurality of dosage times for medicament delivery, (b) translating a tray of a solid dosage medicament dispensing system from a first position within a housing of the solid dosage medicament dispensing system to a second position at least partially outside of the housing, (c) positioning one or more containers in the tray, (d) translating the tray from the second position to the first position, (e) determining an identity of a solid dosage medicament positioned in each of the one or more containers positioned in the tray, and (f) based on the determined identity, providing an option on the user interface to select one or more dosage times corresponding to the plurality of preferred times.

These as well as other aspects, advantages, and alternatives, will become apparent to those of ordinary skill in the art by reading the following detailed description, with reference where appropriate to the accompanying drawings.

BRIEF DESCRIPTION OF THE DRAWINGS

FIG. 6C is a perspective view of a travel tray carrying case, according to an example embodiment.

FIGS. 10A-10M illustrate example user interface prompts, according to example embodiments.

DETAILED DESCRIPTION

Figure 1:
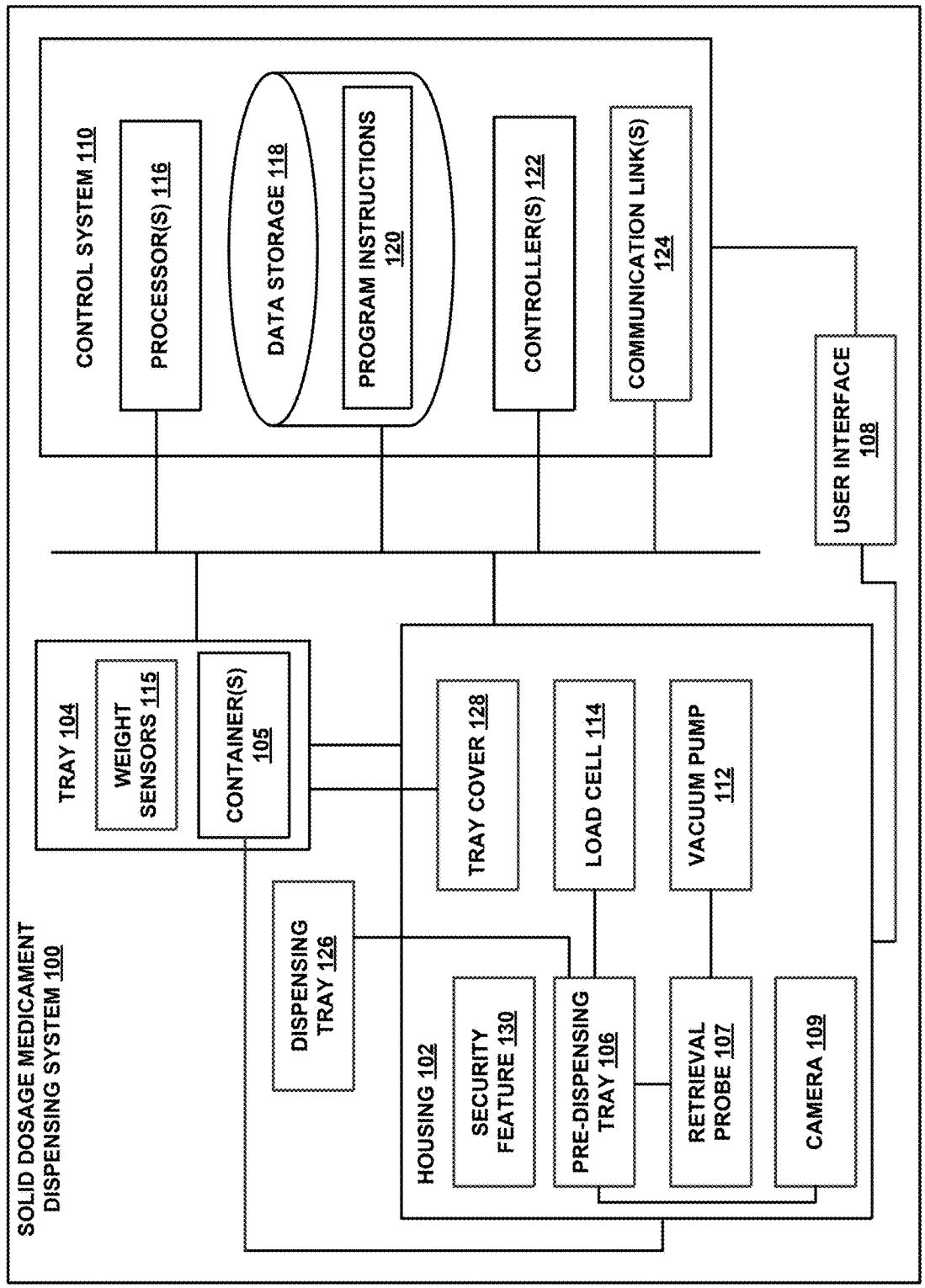
FIG. 1 is a simplified block diagram of an example solid dosage medicament dispensing system, according to an example embodiment.

Example methods and systems are described herein. It should be understood that the words "example," "exemplary," and "illustrative" are used herein to mean "serving as an example, instance, or illustration." Any example or feature described herein as being an "example," being "exemplary," or being "illustrative" is not necessarily to be construed as preferred or advantageous over other examples or features. The examples described herein are not meant to be limiting. It will be readily understood that the aspects of the present disclosure, as generally described herein, and illustrated in the figures, can be arranged, substituted, combined, separated, and designed in a wide variety of different configurations, all of which are explicitly contemplated herein.

Furthermore, the particular arrangements shown in the Figures should not be viewed as limiting. It should be understood that other examples may include more or less of each element shown in a given Figure. Further, some of the illustrated elements may be combined or omitted. Yet further, an example may include elements that are not illustrated in the Figures.

In the following description, numerous specific details are set forth to provide a thorough understanding of the disclosed concepts, which may be practiced without some or all of these particulars. In other instances, details of known devices and/or processes have been omitted to avoid unnecessarily obscuring the disclosure. While some concepts will be described in conjunction with specific examples, it will be understood that these examples are not intended to be limiting.

Unless otherwise indicated, the terms "first," "second," etc. are used herein merely as labels, and are not intended to impose ordinal, positional, or hierarchical requirements on the items to which these terms refer. Moreover, reference to, e.g., a "second" item does not require or preclude the existence of, e.g., a "first" or lower-numbered item, and/or, e.g., a "third" or higher-numbered item.

As used herein, a system, apparatus, structure, article, element, component, or hardware "configured to" perform a specified function is indeed capable of performing the specified function without any alteration, rather than merely having potential to perform the specified function after further modification. In other words, the system, apparatus, structure, article, element, component, or hardware "configured to" perform a specified function is specifically selected, created, implemented, utilized, programmed, and/or designed for the purpose of performing the specified function. As used herein, "configured to" denotes existing characteristics of a system, apparatus, structure, article, element, component, or hardware which enable the system, apparatus, structure, article, element, component, or hardware to perform the specified function without further modification. For purposes of this disclosure, a system, apparatus, structure, article, element, component, or hardware described as being "configured to" perform a particular function may additionally or alternatively be described as being "adapted to" and/or as being "operative to" perform that function.

The limitations of the following claims are not written in means-plus-function format and are not intended to be interpreted based on 35 U.S.C. § 112 (f), unless and until such claim limitations expressly use the phrase "means for" followed by a statement of function void of further structure.

By the term "about," "approximately," or "substantially" with reference to amounts or measurement values described herein, it is meant that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide. For example, in one embodiment, the term "about" can refer to ±10% of a given value.

As used herein, the term "medicament" or "solid dosage medicament" is used herein to refer to a solid medication in the form of a pill, for example, a tablet or a capsule. Any other example of manufactured solid dosage medicament that contains a predetermined or intended amount (e.g., a dose) of a medicinal compound (e.g., a "pharmaceutical" or a "drug") is also considered to be a "medicament," according to the present disclosure. The term "solid," as used herein in the context of a solid medication, refers at least to an exterior surface of the dosage form. Therefore, contemplated medicaments can include liquids, gels, elixirs, solutions, emulsions, and the like that are contained within a solid object such as a hard package (consumable or otherwise) without limitation. It should also be understood that singular referents, e.g., "a pill" or "a medicament" contemplates a plurality of pills and a plurality of medicaments, respectively.

Illustrative, non-exhaustive examples, which may or may not be claimed, of the subject matter according the present disclosure are provided below.

With reference to the Figures, FIG. 1 provides a block diagram of an example solid dosage medicament dispensing system 100. The solid dosage medicament dispensing system 100 is shown for illustrative purposes, and may include more or fewer components. The various components of solid dosage medicament dispensing system 100 may be connected in any manner, including wired and/or wireless connections. Further, in some examples, components of the solid dosage medicament dispensing system 100 may be distributed among multiple physical entities rather than a single physical entity. Other example arrangements of the solid dosage medicament dispensing system 100 are contemplated herein as well.

As shown in FIG. 1, the solid dosage medicament dispensing system 100 includes a housing 102. The solid dosage medicament dispensing system 100 further includes a tray 104 coupled to the housing 102. In one example, the tray 104 is slidably coupled to the housing 102. Other arrangements are possible as well. The tray is configured to receive one or more containers 105. In one example, each of the one or more containers 105 includes a solid dosage medicament. Further, the tray 104 is configured to translate from a first position within the housing 102 to a second position in which the tray 104 is positioned to receive the one or more containers 105. In one example, the tray 104 is positioned entirely within the housing 102 in the first position, and the tray 104 is positioned at least partially outside of the housing 102 in the second position. The tray 104 may be configured to extend out of a front of the housing 102 in the second position, or the tray 104 may be configured to extend out of a side of the housing 102 in the second position. Other arrangements are possible as well.

As shown in FIG. 1, the solid dosage medicament dispensing system 100 further includes a pre-dispensing tray 106. In one example, the pre-dispensing tray 106 may be positioned entirely inside of the housing 102. The solid dosage medicament dispensing system 100 may further include a load cell 114 positioned under the pre-dispensing tray 106. Such a load cell 114 is configured to weigh the contents of the pre-dispensing tray 106 to determine whether or not an appropriate amount of medicament is positioned therein. In another example, the solid dosage medicament dispensing system 100 includes a camera 109 positioned inside the housing 102 and facing the pre-dispensing tray 106 to take picture of the contents of the pre-dispensing tray 106 to determine whether or not an appropriate amount of medicament is positioned therein. Other ways to verify that an appropriate amount of medicament is positioned in the pre-dispensing tray 106 are possible, as discussed in additional detail below.

The solid dosage medicament dispensing system 100 further includes a retrieval probe 107 moveable between the one or more containers 105 and the pre-dispensing tray 106. In one example, the retrieval probe 107 may be positioned entirely inside of the housing 102. In one example, the solid dosage medicament dispensing system 100 further includes a vacuum pump 112 in communication with the retrieval probe 107 and configured to create a negative pressure within the retrieval probe 107. Such an arrangement enables the retrieval probe 107 to pick up or capture and move a single solid dosage medicament, as discussed in additional detail below. Other arrangements of the retrieval probe 107 for transporting a solid dosage medicament are possible as well.

The solid dosage medicament dispensing system 100 may further include a dispensing tray 126 removably coupled to the housing 102. The dispensing tray 126 is configured to receive a solid dosage medicament from the pre-dispensing tray 106. In another embodiment, the dispensing tray 126 can be configured to receive a solid dosage medicament directly from the retrieval probe 107. The dispensing tray 126 may be removably coupled to an exterior of the housing 102, while the pre-dispensing tray 106 is positioned within the housing 102. The dispensing tray 126 may include a tab extending in a direction away from the housing 102. Such a tab provides a surface for a user to grasp and remove the dispensing tray 126 from the housing 102. In one example, the dispensing tray 126 is removably coupled to the housing 102 via one or more magnets. Other temporary coupling mechanisms or combinations of mechanisms are possible as well.

Further, the solid dosage medicament dispensing system 100 may include a tray cover 128 removably positioned over the tray 104 to cover the one or more containers 105 positioned in the tray 104. As such, the one or more containers 105 may be positioned in the tray 104 without a cap or other closure, and the tray cover 128 is used to cover the one or more containers 105 positioned in the tray 104. This arrangement may help prevent solid dosage medicaments positioned in the one or more containers 105 from spilling in the event that the solid dosage medicament dispensing system 100 tips over or is otherwise disturbed from the intended upright position. This arrangement may also help preserve the integrity of solid dosage medicaments positioned in the one or more containers 105 positioned in the tray 104. In one example, the tray cover 128 comprises a plurality (e.g., a pair) of doors that open so that the retrieval probe 107 can access the contents of the one or more containers 105. In another example, the tray cover 128 comprises a spring-loaded retractable cover. In one embodiment, the tray 104 can be configured to form a seal with the one or more containers 105 positioned in the tray 104. Other arrangements for the tray cover 128 are possible as well.

The solid dosage medicament dispensing system 100 further includes a user interface 108 configured to receive one or more inputs from a user. The user interface 108 may comprise a finger-operable touchscreen and/or may include one or more buttons and/or sensors for receiving the one or more inputs from the user. In one example, the user interface 108 (e.g., touchscreen) can articulate so as to change the angle of the user interface with respect to the user. Such a touchscreen may be used by a user to input commands to the solid dosage medicament dispensing system 100. To this end, the touchscreen may be configured to sense at least one of a position and a movement of a user's finger via capacitive sensing, resistance sensing, or a surface acoustic wave process, among other possibilities. The touchscreen may be capable of sensing finger movement in a direction parallel or planar to the touchscreen surface, in a direction normal to the touchscreen surface, or both, and may also be capable of sensing a level of pressure applied to the touchscreen surface. The touchscreen may be formed of one or more translucent or transparent insulating layers and one or more translucent or transparent conducting layers. The touchscreen may take other forms as well. Further, in some examples, the touchscreen may be configured as a display for providing output from various components of the solid dosage medicament dispensing system 100.

The user interface 108 may further include or be associated with one or more microphones and/or one or more speakers. The microphone(s) may be configured to receive audio (e.g., a voice command or other audio input) from a user of the solid dosage medicament dispensing system 100. Similarly, the speaker(s) may be configured to output audio to the user of the solid dosage medicament dispensing system 100. In one particular example, the user interface 108 may be set up for wireless communications with a medical professional (either via a video conference or audio conference) to answer questions regarding the solid dosage medicament in the solid dosage medicament dispensing system 100.

The solid dosage medicament dispensing system 100 may further include a security feature 130, which may require an input from the user or a remote user (e.g., a caregiver, a family member of the user, a doctor, or a pharmacist) prior to enabling the user interface 108 to receive one or more inputs from the user. As non-limiting examples, the security feature 130 may comprise a fingerprint scanner, a retina scanner, a camera, and/or a pin pad. The security feature 130 may be separate from the user interface 108, or may be an integral component of the user interface 108.

Further still, the solid dosage medicament dispensing system 100 includes a control system 110 configured to perform one or more functions of the solid dosage medicament dispensing system 100 based on the one or more inputs received from the user. As shown in FIG. 1, the control system 110 may include processor(s) 116, data storage 118, controller(s) 122, and communication link(s) 124. Processor(s) 116 may operate as one or more general-purpose hardware processors or special purpose hardware processors (e.g., digital signal processors, application specific integrated circuits, etc.). The processor(s) 116 may be configured to execute computer-readable program instructions 120 stored in the data storage 118. The processor(s) 116 may also directly or indirectly interact with other components of the solid dosage medicament dispensing system 100, such as the retrieval probe 107, vacuum pump 112, tray cover 128, load cell 114, user interface 108, security feature 130, and/or communication link(s) 124.

The data storage 118 may be one or more types of hardware memory. For example, the data storage 118 may include or take the form of one or more computer-readable storage media that can be read or accessed by processor(s) 116. The one or more computer-readable storage media can include volatile and/or non-volatile storage components, such as optical, magnetic, organic, or another type of memory or storage, which can be integrated in whole or in part with processor(s) 116. In some implementations, the data storage 118 can be a single physical device. In other implementations, the data storage 118 can be implemented using two or more physical devices, which may communicate with one another via wired or wireless communication. As noted previously, the data storage 118 may include the computer-readable program instructions 120, as well as additional data. The additional data may be any type of data, such as configuration data, sensor data, and/or diagnostic data, among other possibilities.

The controller(s) 122 may include one or more electrical circuits, units of digital logic, computer chips, and/or microprocessors that are configured to (perhaps among other tasks) interface between any combination of the retrieval probe 107, vacuum pump 112, tray cover 128, load cell 114, user interface 108, security feature 130, communication link(s) 124, and/or a user of the solid dosage medicament dispensing system 100. In some implementations, the controller(s) 122 may be a purpose-built embedded device for performing specific operations with one or more subsystems of the solid dosage medicament dispensing system 100.

The control system 110 may monitor and physically change the operating conditions of the solid dosage medicament dispensing system 100. In doing so, the control system 110 may serve as a link between portions of the solid dosage medicament dispensing system 100, such as between the user interface 108 and the retrieval probe 107, between the retrieval probe and the one or more containers 105, between the solid dosage medicament dispensing system 100 and another computing device, and/or or between the solid dosage medicament dispensing system 100 and a user, as non-limiting examples. The example interfaces and communications noted above may be implemented via a wired or wireless connection, or both. The control system 110 may perform other operations for the solid dosage medicament dispensing system 100 as well.

In some implementations, the control system 110 of solid dosage medicament dispensing system 100 may also include communication link(s) 124 configured to send and/or receive information. The communication link(s) 124 may transmit data indicating the state of the various components of the solid dosage medicament dispensing system 100. For example, information read by the retrieval probe 107 or load cell 114 may be transmitted via the communication link(s) 124 to a separate device. Other diagnostic information indicating the integrity or health of the various components of the solid dosage medicament dispensing system 100 may be transmitted via the communication link(s) 124 to an external communication device. Further, data such as missed dosages or other patient compliance statistics with respect to the scheduled medicament delivery of a solid dosage medicament using the solid dosage medicament dispensing system 100 may be transmitted via the communication link(s) 124 to a separate device.

In some implementations, the solid dosage medicament dispensing system 100 may receive information at the communication link(s) 124 that is then processed by the processor(s) 116. The received information may indicate data that is accessible by the processor(s) 116 during execution of the computer-readable program instructions 120. Further, the received information may change aspects of the controller(s) 122 that may affect the behavior of one or more components of the solid dosage medicament dispensing system 100.

In some cases, the communication link(s) 124 may include a wired connection. The solid dosage medicament dispensing system 100 may include one or more ports to interface the communication link(s) 124 to an external device. The communication link(s) 124 may include, in addition to or as an alternative to the wired connection, a wireless connection. Some example wireless connections may utilize a cellular connection, such as CDMA, EVDO, GSM/GPRS, or 4G telecommunication, such as WiMAX or LTE. Alternatively or in addition, the wireless connection may utilize a Wi-Fi connection to transmit data to a wireless local area network (WLAN). In some implementations, the wireless connection may also communicate over an infrared link, Bluetooth, or a near-field communication (NFC) device.

Operations of the control system 110 may be carried out by the processor(s) 116. Alternatively, these operations may be carried out by the controller(s) 122, or a combination of the processor(s) 116 and the controller(s) 122. In some implementations, the control system 110 may partially or wholly reside on a device other than the solid dosage medicament dispensing system 100, and therefore may, at least in part, control the solid dosage medicament dispensing system 100 remotely. The communication link(s) 124 may be used, at least in part, to carry out the remote communication. In other implementations, the control system wholly resides in the solid dosage medicament dispensing system 100.

During operation, the control system 110 may communicate with other systems of the solid dosage medicament dispensing system 100 via wired or wireless connections, and may further be configured to communicate with one or more users of the solid dosage medicament dispensing system 100. As one possible illustration, the control system 110 may receive an input (e.g., from a user) indicating an instruction to perform a particular set of one or more tasks. The input to control system 110 may be received via the user interface 108. Based on this input, the control system 110 may perform operations to cause the solid dosage medicament dispensing system 100 to perform one or more tasks.

In particular, the control system 110 may be configured to (i) determine an identity of a solid dosage medicament positioned in a container 105 of the one or more containers positioned in the tray 104, and (ii) provide an option on the user interface 108 to select a dosage time based on the determined identity. In one particular example, an exterior surface of each of the one or more containers 105 includes a unique identifier configured to provide an identity of a solid dosage medicament positioned in the container 105. The unique identifier may comprise a barcode, a Quick Response (QR) code, a radio frequency identification (RFID), a near-field communication (NFC), or a mechanical pin or other configuration, as non-limiting examples. The solid dosage medicament dispensing system 100, in turn, includes a reader configured to read the unique identifier of the one or more containers 105. In one example, the reader comprises a camera (not shown) on an exterior of the housing 102 of the solid dosage medicament dispensing system 100. In such an example, the reader identifies the solid dosage medicament prior to the container 105 being positioned in the tray 104. In another example, the reader is positioned in the tray 104 such that the reader identifies the solid dosage medicament when the container 105 is positioned in the tray 104. In yet another example, the reader may comprise a camera on a smartphone of the user. In any case, the reader may be in communication with the control system 110, and the control system 110 can process the data received from the reader to thereby determine the identity of the solid dosage medicament positioned in the one or more container 105. In yet another example, the user inputs medication information directly into the user interface 108.

In another example, the control system 110 may be configured to (i) vibrate the tray 104 (e.g., via a vibration motor positioned in the housing 102), (ii) move the retrieval probe 107 to a location above a container 105 of the one or more containers positioned in the tray 104, (iii) lower the retrieval probe 107 into the container 105 to capture a solid dosage medicament from the container 105 (e.g., via a suction from the vacuum pump 112), and (iv) determine whether the retrieval probe 107 has captured the solid dosage medicament. The step of determining whether the retrieval probe 107 has captured the solid dosage medicament may comprise (i) comparing a detected vacuum reading of the retrieval probe to a threshold level, (ii) if the detected vacuum reading is less than the threshold level, determining that the retrieval probe 107 has captured the solid dosage medicament, and (iii) if the detected vacuum reading is not less than the threshold level, determining that the retrieval probe 107 has not captured the solid dosage medicament. In another example, a change in pressure may be measured to determine whether or not the retrieval probe 107 has captured the solid dosage medicament from the container 105. In another example, the tray 104 may include weight sensors 115 to verify the weight taken out of the container 105 matches the weight determined by the load cell 114 in the pre-dispensing tray 106. Other example methods for determining whether the retrieval probe 107 has captured the solid dosage medicament are possible as well.

The control system 110 may be further configured, in response to a determination that the retrieval probe 107 has not captured the solid dosage medicament, to adjust a lateral position of the retrieval probe 107. Additionally or alternatively, the control system 110 may further cause the tray 104 to vibrate in response to a determination that the retrieval probe 107 has not captured the solid dosage medicament. In one example, adjusting the lateral position of the retrieval probe 107 comprises initially lowering the retrieval probe 107 into a first position in the container 105 and moving the retrieval probe 107 in a spiral direction from the first position until a determination is made that the retrieval probe 107 has captured the solid dosage medicament. In one such example, the first position is in the middle of the container 105. In another example, the adjusting the lateral position of the retrieval probe 107 comprises initially lowering the retrieval probe 107 into a first position in the container 105 and moving the retrieval probe 107 in a random path from the first position until a determination is made that the retrieval probe 107 has captured the solid dosage medicament.

In another example, the control system 110 is further configured to (i) move the retrieval probe 107 to the pre-dispensing tray 106 in response to a determination that the retrieval probe 107 has captured the solid dosage medicament from a container 105, and (ii) release the solid dosage medicament from the retrieval probe 107 into the pre-dispensing tray 106. In one such example, the control system 110 is further configured to, (i) if a user input is received at the user interface 108, dispense the solid dosage medicament to an exterior of the housing 102, and (ii) if no user input is received at the user interface 108 within a threshold time period, (a) move the retrieval probe 107 to the pre-dispensing tray 106, (b) capture the solid dosage medicament from the pre-dispensing tray 106, and (c) return the solid dosage medicament to the container 105. Such an arrangement ensures that the solid dosage medicament is positioned within the housing 102 (and therefore inaccessible) until a user provides a user input to dispense the solid dosage medicament.

Figure 2:
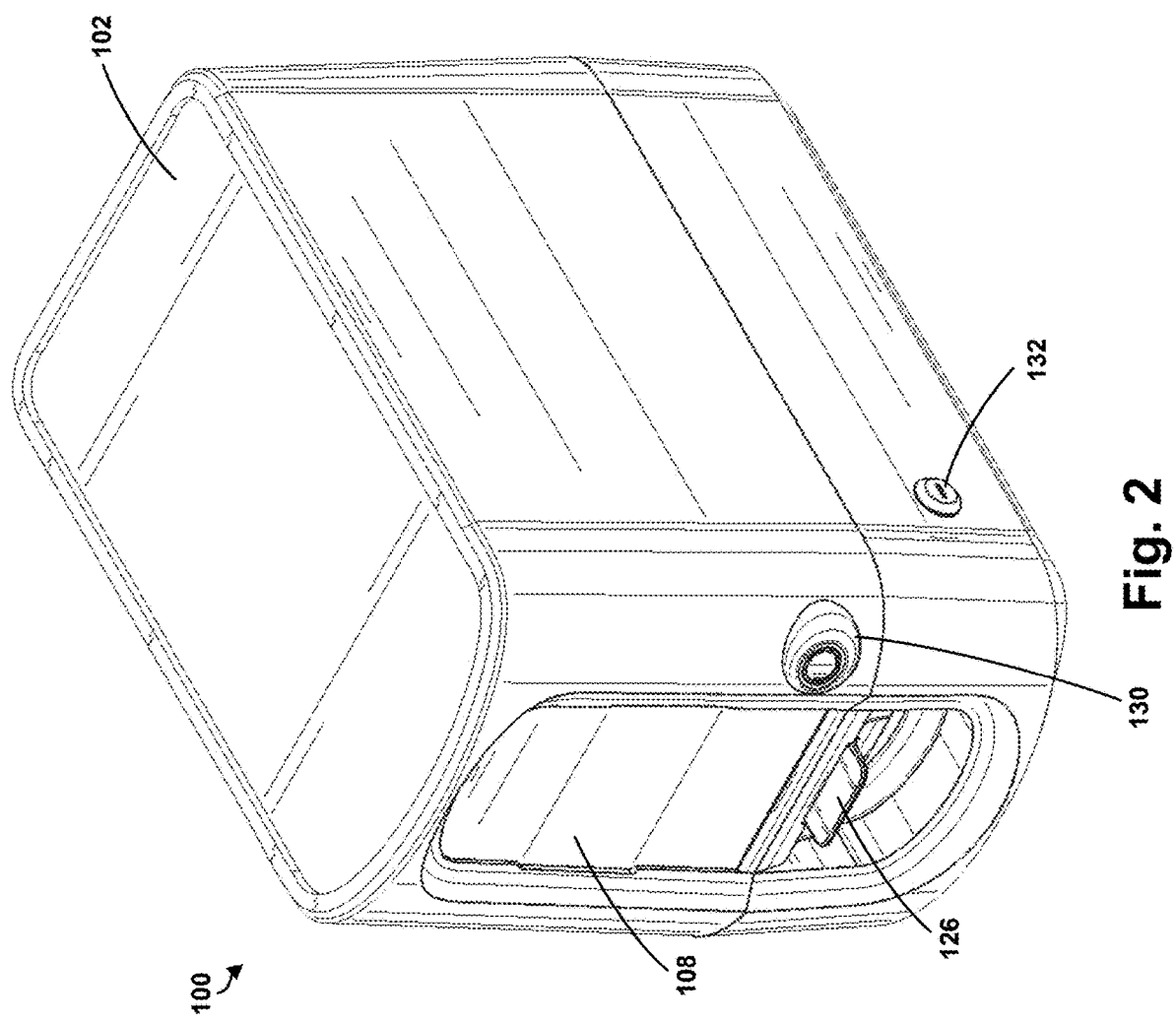
FIG. 2 is a perspective view of the solid dosage medicament dispensing system, according to an example embodiment.

FIG. 2 illustrates a perspective view of the solid dosage medicament dispensing system 100. In particular, FIG. 2 illustrates the housing 102, the user interface 108, the dispensing tray 126, and the security feature 130. FIG. 2 further illustrates a lock 132 which may be included to maintain the tray 104 in the first position within the housing 102. When the lock 132 is unlocked (e.g., via a corresponding key), the tray 104 can then transition from the first position to a second position outside of the housing 102 so that the tray 104 can receive one or more containers 105.

Figure 3:
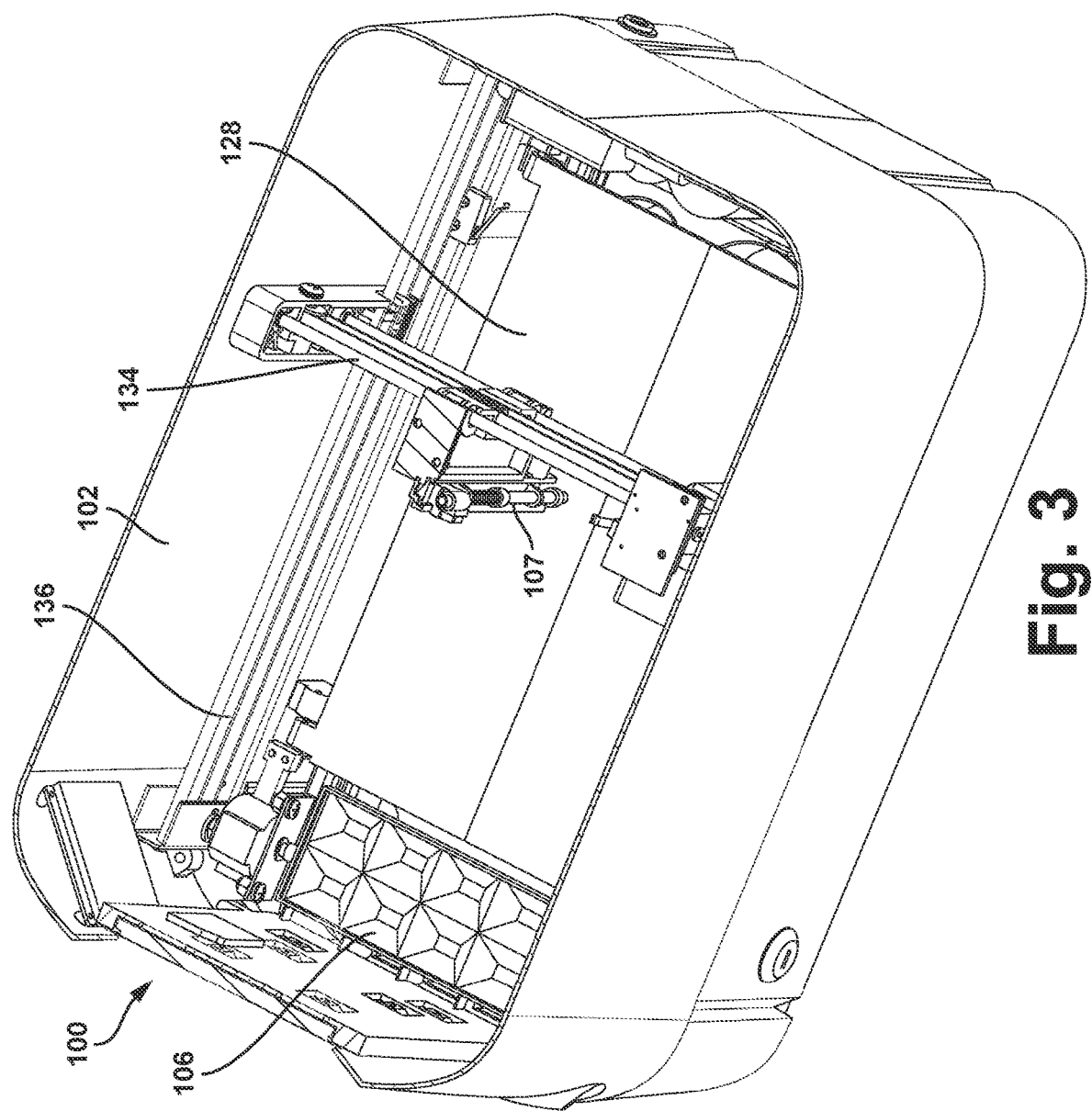
FIG. 3 is a perspective cross-sectional view of the solid dosage medicament dispensing system of FIG. 2, according to an example embodiment.

FIG. 3 illustrates a perspective cross-sectional view of the solid dosage medicament dispensing system 100. In particular, FIG. 3 illustrates the housing, the pre-dispensing tray 106, the retrieval probe 107, and the tray cover 128. As shown in FIG. 3, the tray cover 128 is in a closed position covering the one or more containers 105 positioned in the tray 104. As shown in FIG. 3, the solid dosage medicament dispensing system 100 may further include a gantry 134 coupled to the retrieval probe 107. The gantry 134 may be positioned on a track 136 that runs along at least a portion of each side of the housing 102. In use, the gantry 134 can move forward and backward along the track 136, and the retrieval probe 107 can move side to side along the gantry 134. Thus, the gantry 134 and track 136 together provide the x-y axis movement of the retrieval probe 107. The retrieval probe 107 may be further configured to move up and down, giving the retrieval probe 107 its z-axis movement.

Figure 4:
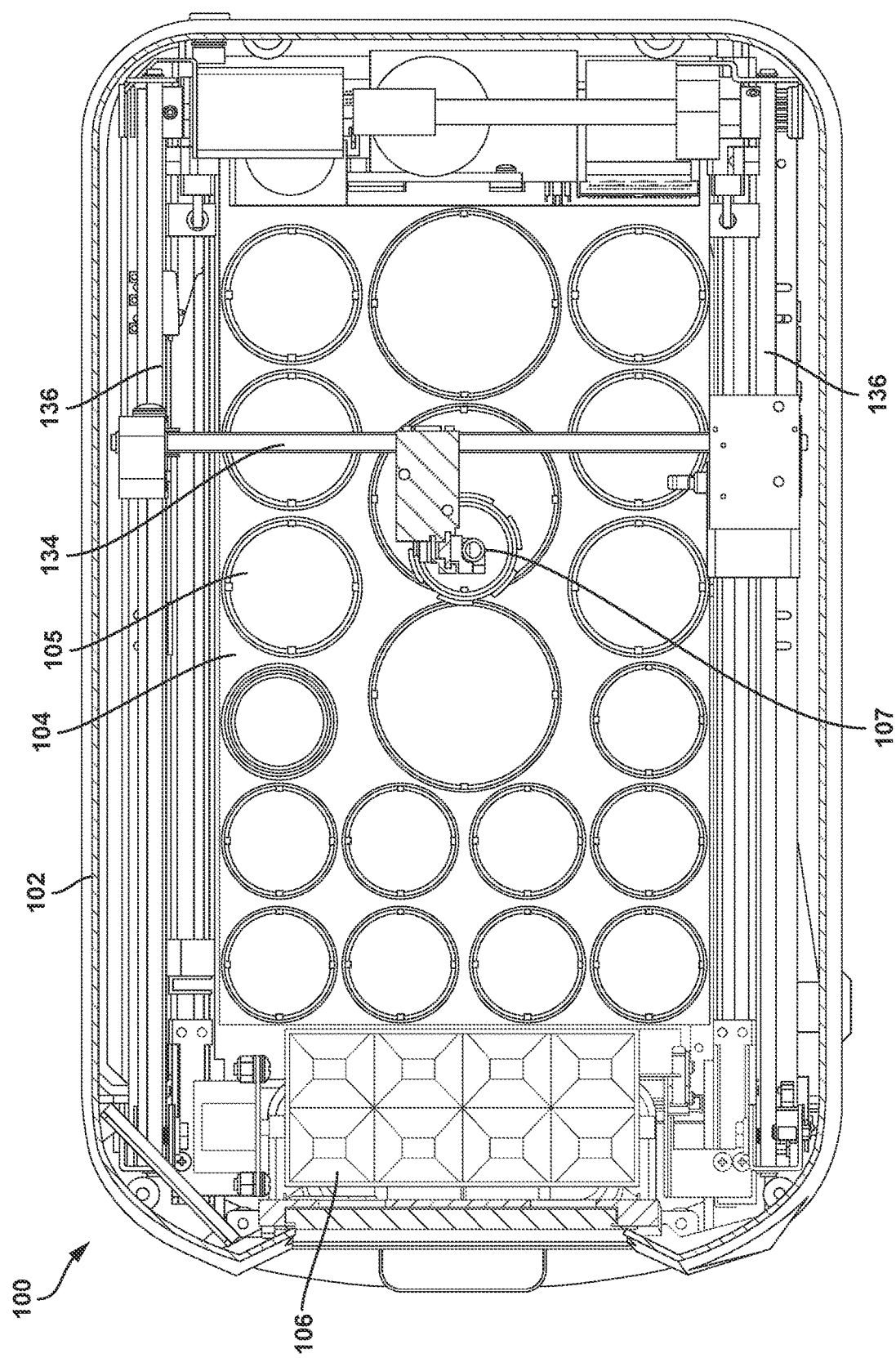
FIG. 4 is a top cross-sectional view of the solid dosage medicament dispensing system of FIG. 2, according to an example embodiment.

FIG. 4 illustrates a top cross-sectional view of the solid dosage medicament dispensing system 100. In particular, FIG. 4 illustrates a view with the tray cover 128 in a retracted position, such that the one or more containers 105 (here shown in varying sizes) in the tray 104 are accessible by the retrieval probe 107.

Figure 5C:
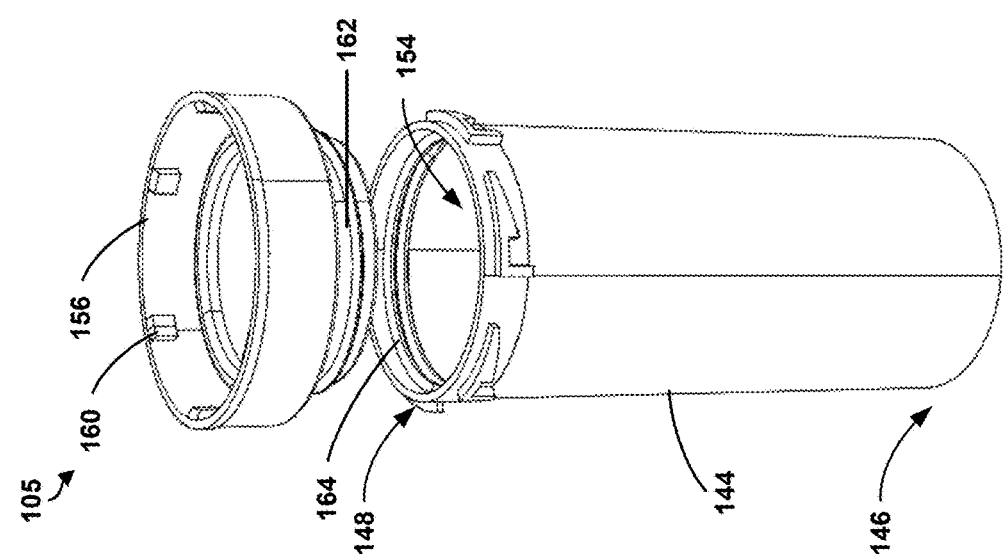
FIG. 5C is a perspective view of the container of FIG. 5A, according to an example embodiment.
Figure 5B:
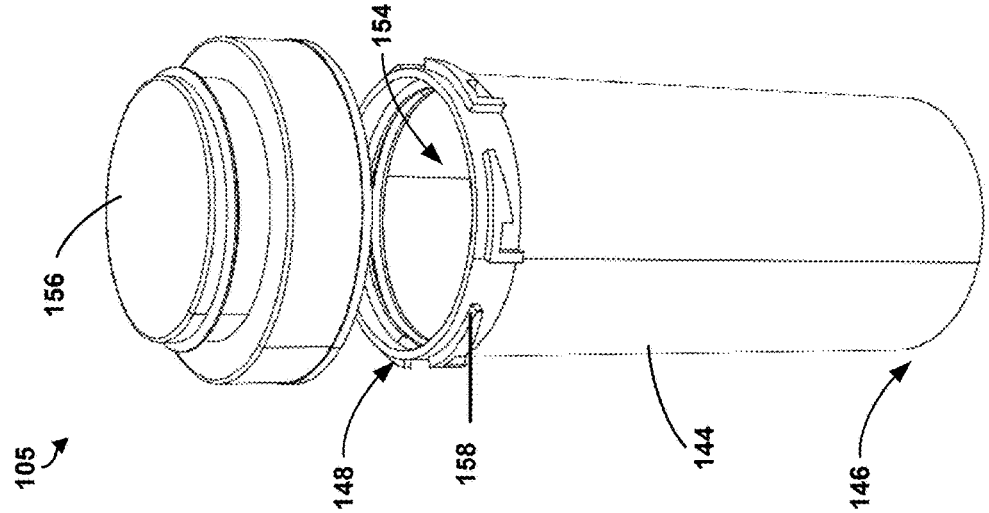
FIG. 5B is a perspective view of the container of FIG. 5A, according to an example embodiment.
Figure 5A:
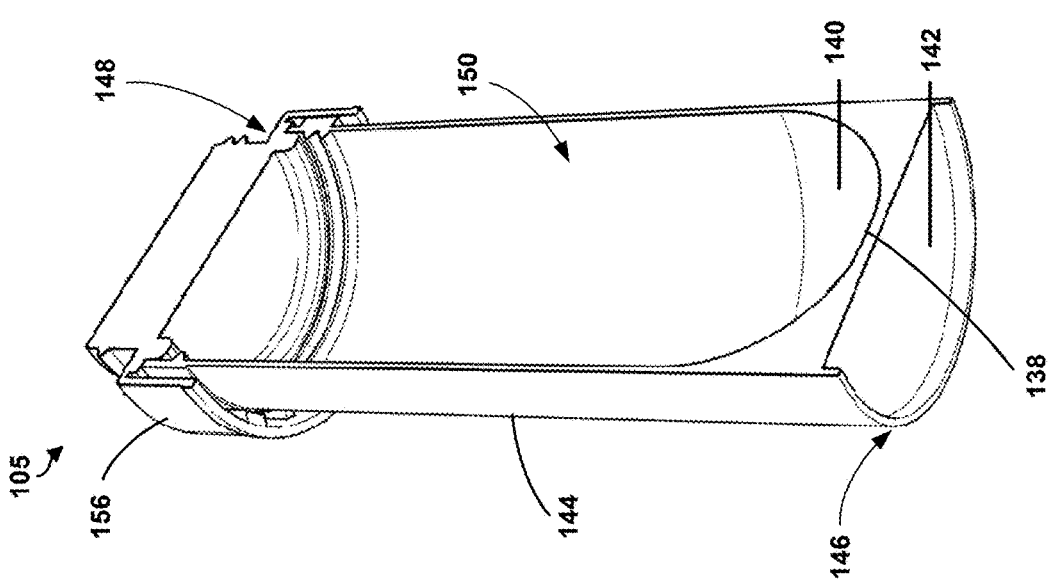
FIG. 5A is a cross-sectional view of a container, according to an example embodiment.

FIG. 5A illustrates a cross-sectional view of a container 105, according to an example embodiment. As discussed above, the container 105 may be configured to be positioned within the tray 104 of the solid dosage medicament dispensing system 100. As shown in FIG. 5, the container 105 comprises a base 138 having an interior surface 140 and an exterior surface 142. The interior surface 140 of the base 138 has a radius of curvature greater than zero. This curved interior surface 140 of the base 138 of the container 105 may help to position the solid dosage medicament to the center of the interior surface 140 of the base 138, thereby making pill retrieval by the retrieval probe 107 easier. In use, the tray 104 may be vibrated, which along with the curved interior surface 140 of the base 138, will further help position the solid dosage medicament to the center of the interior surface 140 of the base 138. The exterior surface 142 of the base may be substantially flat, as shown in FIG. 5A. Such an arrangement may ease the positioning of a unique identifier thereon. Such a unique identifier may be configured to provide an identity of a solid dosage medicament positioned in the container 105. As discussed above, the unique identifier may comprise a barcode, a QR code, an RFID, an NFC, or a mechanical pin, as non-limiting examples. In another embodiment (not shown), the exterior surface may have a mechanical configuration (e.g., pattern and/or shape) that serves as a unique identifier. The solid dosage medicament dispensing system 100, in turn, includes a reader configured to read the unique identifier of the one or more containers 105. The reader may be in communication with the control system 110, and the control system 110 can process the data received from the reader to thereby determine the identity of the solid dosage medicament positioned in a container 105.

The container 105 further includes a sidewall 144 having a first end 146 coupled to the base 138 and a second end 148 opposite the first end 146. An interior surface 150 of the sidewall 144 and the interior surface 140 of the base 138 define a chamber 152 therebetween. The second end 148 of the sidewall 144 defines an opening 154. The container 105 further includes a removable cap 156 removably coupled to the second end 148 of the sidewall 144 to thereby cover the opening 154.

FIG. 5B illustrates a perspective view of the container 105 of FIG. 5A, according to an example embodiment. As shown in FIG. 5B, the removable cap 156 has been removed from the container 105 to expose the opening 154. The second end 148 of the sidewall 144 may include a plurality of tamper-proof features 158 that lock with corresponding tamper-proof features 160 of the removable cap 156 (as shown in FIG. 5C).

FIG. 5C illustrates another perspective view of the container 105 of FIG. 5A, according to an example embodiment. As shown in FIG. 5C, the removable cap 156 can be flipped 180 degrees and reattached to the container 105 for easy access screwing and unscrewing. In particular, the top of the removable cap 156 includes a thread 162 that is configured to interact with a corresponding thread 164 of the second end 148 of the sidewall 144.

Figure 6A:
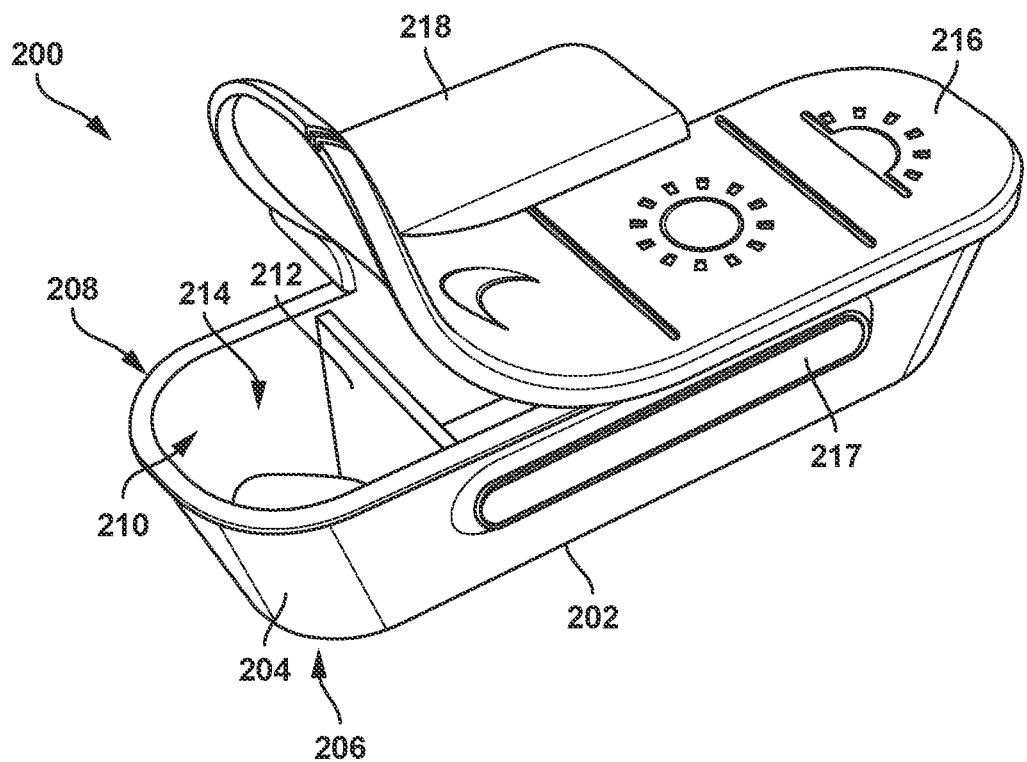
FIG. 6A is a perspective view of a travel tray, according to an example embodiment.

FIG. 6A illustrates a perspective view of a travel tray 200, according to an example embodiment. The travel tray 200 includes a base 202 having an interior surface and an exterior surface. The travel tray 200 further includes a sidewall 204 having a first end 206 coupled to the base 202 and a second end 208 opposite the first end 206. The second end 208 of the sidewall 204 defines an opening 210. The travel tray 200 further includes one or more dividers 212 each coupled to the interior surface of the base 202 and an interior surface of the sidewall 204. The interior surface of the sidewall 204, the interior surface of the base 202, and the plurality of dividers 212 define a plurality of chambers 214 therebetween. The travel tray 200 further includes a removable cover 216 removably coupled to the second end 208 of the sidewall 204 to thereby cover the opening 210. The removable cover 216 includes a visual indication of a time of day positioned over each of the plurality of chambers 214 when the removable cover 216 is positioned over the opening 210. The sidewall 204 may further include a metal strip 217 or other coupling device that is used to removably couple the travel tray 200 to the housing 102 of the solid dosage medicament dispensing system 100.

Figure 6B:
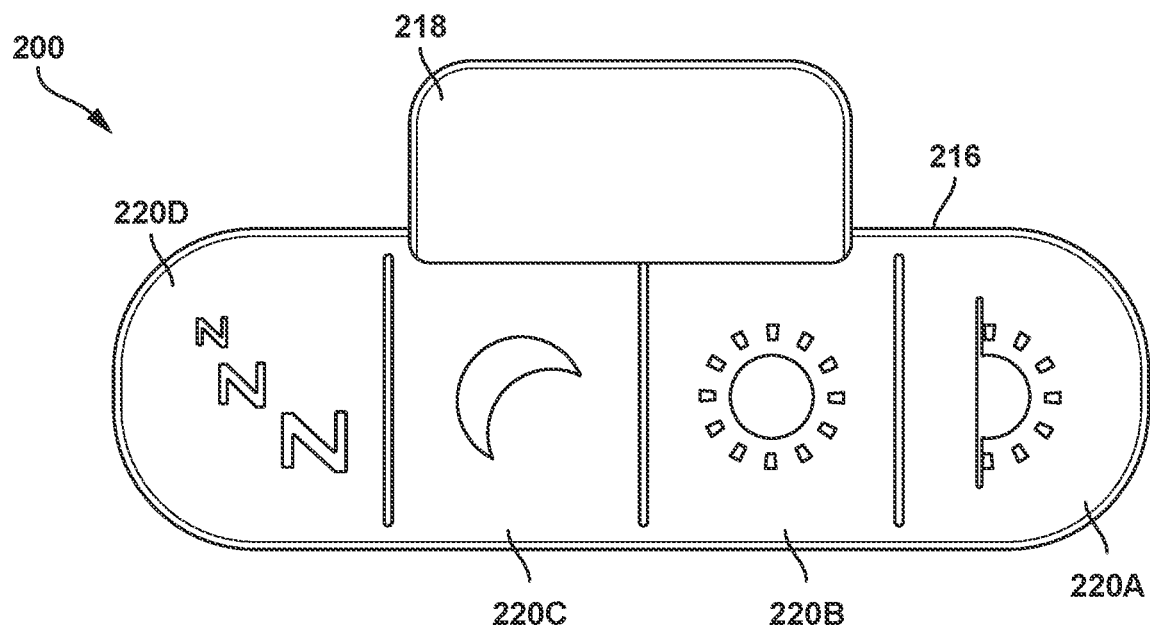
FIG. 6B is a top view of the travel tray of FIG. 6A, according to an example embodiment.

In one example, the removable cover further includes a tab 218 with a visual indication of a day of the week. In one particular example, as shown in FIGS. 6A-6B the one or more dividers 212 comprises three dividers to thereby define four chambers 214. Further, as illustrated in the top view of FIG. 6B, in one example, the visual indication of a time of day on the removable cover 216 comprises a morning visual indication 220A, a mid-day visual indication 220B, an evening visual indication 220C, and a bedtime visual indication 220D.

In use, the travel tray 200 may be removably coupled to the housing 102 of the solid dosage medicament dispensing system 100 as discussed above. The user may provide an input into the user interface 108 indicating a length of time the user will be away from home, and the user interface 108 may provide prompts to removably couple one or more travel trays 200 corresponding to the one or more days the user will be away from home. The solid dosage medicament dispensing system 100 may be configured to cause the pre-dispensing tray 106 to move aside, and the retrieval probe 107 may be configured to directly place the solid dosage medicament into the chambers 214 of the travel tray 200. The retrieval probe 107 is configured to position the solid dosage medicament into a particular chamber of the plurality of chambers 214 based on the identity of the solid dosage medicament and the time of day the user selected to take the solid dosage medicament.

FIG. 6C illustrates a travel tray carrying case 222, according to an example embodiment. As shown in FIG. 6C, the travel tray carrying case 222 includes a plurality of slots to receive a plurality of travel trays 200, and a zipper 224 configured to close the travel tray carrying case 222. Other closure mechanisms are contemplated as well.

Figure 7:
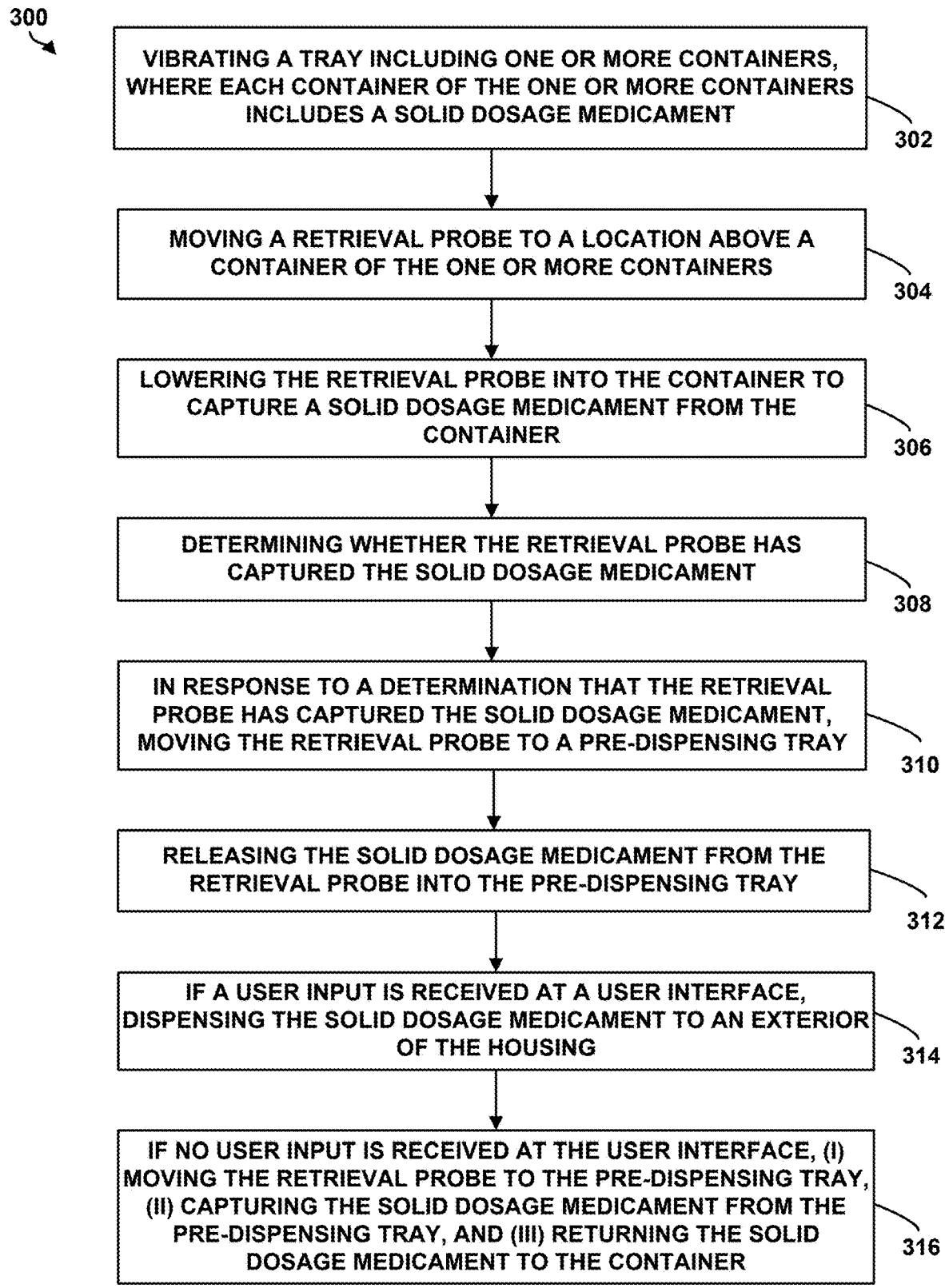
FIG. 7 is a flowchart of an example method, according to an example embodiment.

FIG. 7 is a block diagram of an example of a method 300. Method 300 shown in FIG. 7 presents an embodiment of a method that could be used with any of the systems or devices described above in relation to FIGS. 1-6C, as an example. Method 300 includes one or more operations, functions, and/or actions as illustrated by one or more of blocks 302-316. Although the blocks are illustrated in a sequential order, these blocks may also be performed in parallel, and/or in a different order than those described herein. Also, the various blocks may be combined into fewer blocks, divided into additional blocks, and/or removed based upon the desired implementation.

In addition, for the method 300 and other processes and methods disclosed herein, the block diagram shows functionality and operation of one possible implementation of present embodiments. In this regard, the method 300 can be caused to be performed by program code, which includes one or more instructions executable by a processor or computing device for implementing specific logical functions or steps in the process. The program code may be stored on any type of computer readable medium, for example, such as a storage device including a disk or hard drive. The computer readable medium may include a non-transitory computer readable medium, for example, such as one or more computer-readable media that store data for short periods of time like register memory, processor cache, and Random Access Memory (RAM). The computer readable medium may also include non-transitory media, such as secondary or persistent long term storage, like read only memory (ROM), optical or magnetic disks, and compact-disc read only memory (CD-ROM), for example. The computer readable medium may also be any other volatile or non-volatile storage systems. The computer readable medium may be considered a computer readable storage medium, for example, or a tangible storage device.

In addition, for the method 300 and other processes and methods disclosed herein, each block in FIG. 7 may represent circuitry that is wired or otherwise functionally connected to perform the specific logical functions in the process.

Initially, at block 302, the method 300 includes vibrating a tray including one or more containers, where each container of the one or more containers includes a solid dosage medicament. At block 304, the method 300 includes moving a retrieval probe to a location above a container of the one or more containers. At block 306, the method 300 includes lowering the retrieval probe into the container to capture a solid dosage medicament from the container. At block 308, the method 300 includes determining whether the retrieval probe has captured the solid dosage medicament. At block 310, the method 300 includes, in response to a determination that the retrieval probe has captured the solid dosage medicament, moving the retrieval probe to a pre-dispensing tray. At block 312, the method 300 includes releasing the solid dosage medicament from the retrieval probe into the pre-dispensing tray. At block 314, the method 300 includes, if a user input is received at a user interface, dispensing the solid dosage medicament to an exterior of the housing. At block 316, the method 300 includes, if no user input is received at the user interface, (i) moving the retrieval probe to the pre-dispensing tray, (ii) capturing the solid dosage medicament from the pre-dispensing tray, and (iii) returning the solid dosage medicament to the container. In another example, instead of returning the solid dosage medicament to the container, the method 300 may include transporting the solid dosage medicament to a different container or other pill disposal area.

In one example, the step in the method 300 of determining whether the retrieval probe has captured the solid dosage medicament comprises (a) comparing a detected vacuum reading of the retrieval probe to a threshold level, (b) if the detected vacuum reading is less than the threshold level, determining that the retrieval probe has captured the solid dosage medicament, and (c) if the detected vacuum reading is not less than the threshold level, determining that the retrieval probe has not captured the solid dosage medicament.

In another example, the method 300 further includes (a) after releasing the solid dosage medicament from the retrieval probe into the pre-dispensing tray, determining a weight of the contents of the pre-dispensing tray, and (b) if the determined weight exceeds a threshold, (i) moving the retrieval probe to the pre-dispensing tray, (ii) capturing an extra solid dosage medicament from the pre-dispensing tray, and (iii) returning the extra solid dosage medicament to the container.

Figure 8A:
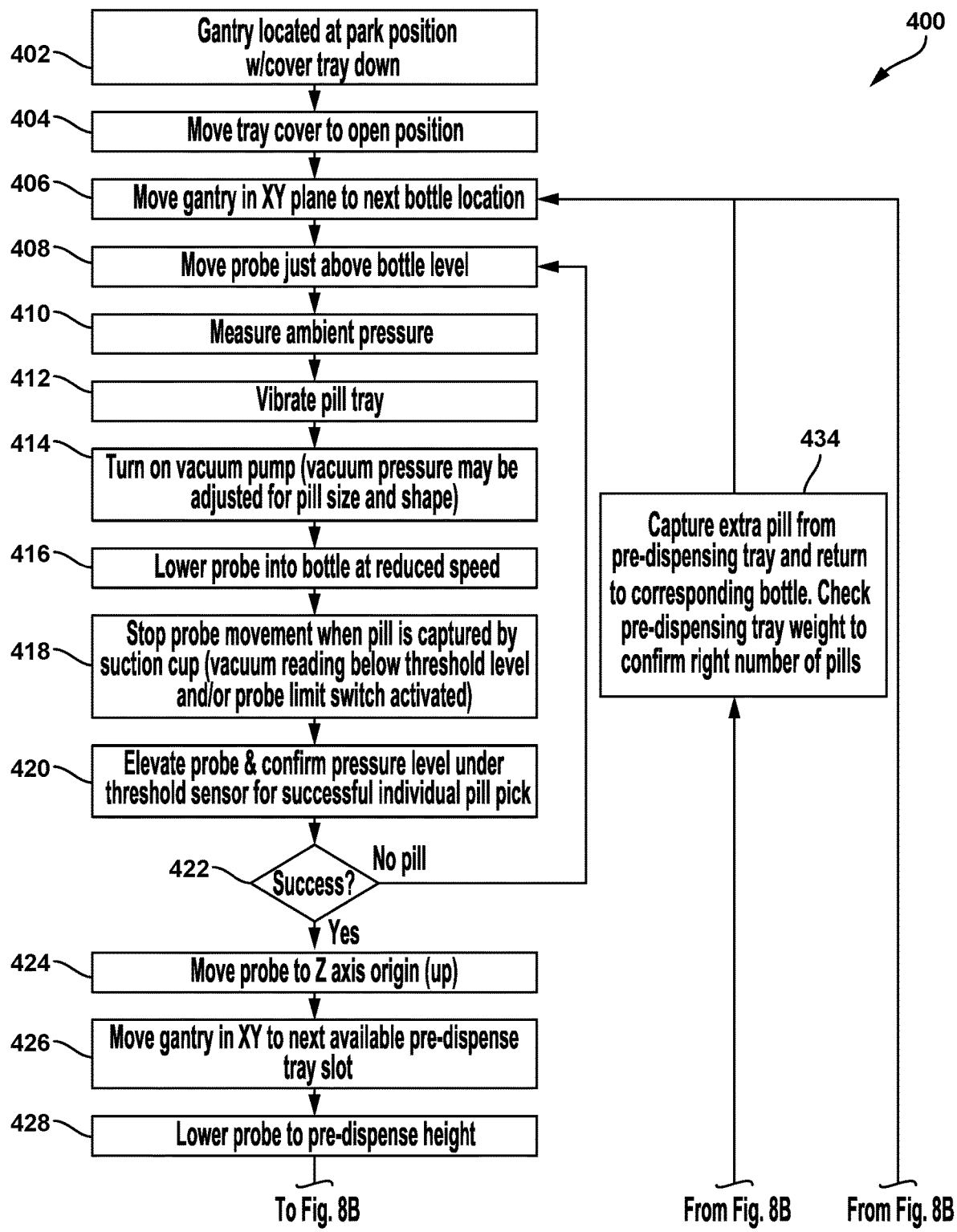
FIGS. 8A-8B is a flowchart of another example method, according to an example embodiment.
Figure 8B:
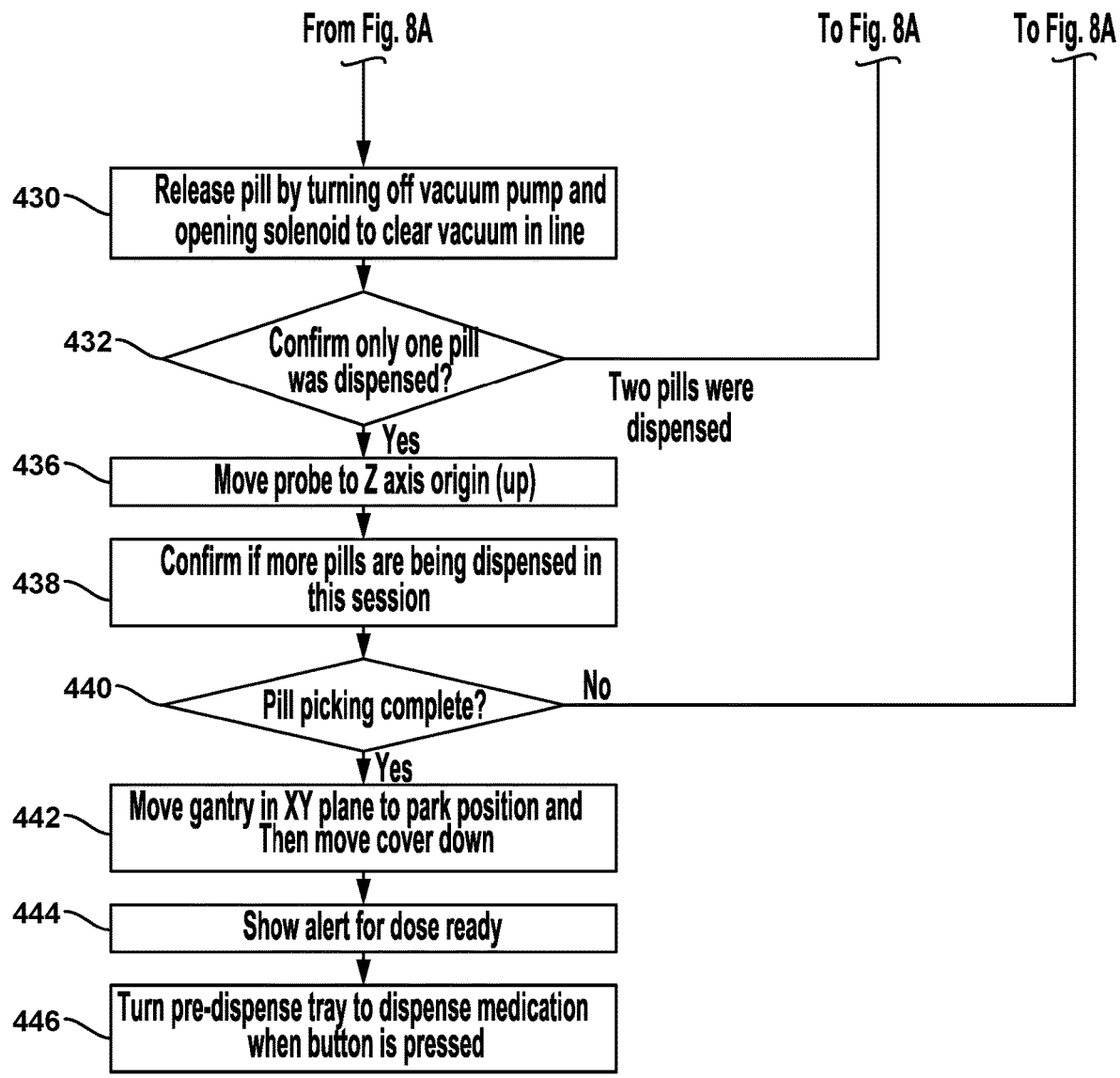

FIGS. 8A-8B is a block diagram of an example of a method 400. Method 400 shown in FIGS. 8A-8B presents an embodiment of a method that could be used with any of the systems or devices described above in relation to FIGS. 1-6C, as an example. Method 400 includes one or more operations, functions, and/or actions as illustrated by one or more of blocks 402-446, which when performed in concert can be considered a dispensing session. Although the blocks are illustrated in a sequential order, these blocks may also be performed in parallel, and/or in a different order than those described herein. Also, the various blocks may be combined into fewer blocks, divided into additional blocks, and/or removed based upon the desired implementation.

Initially, at block 402, the method 400 includes positioning the gantry at a park position with the tray cover down. At block 404, the method 400 includes moving the tray cover to an open position. At block 406, the method 400 includes moving the gantry in an xy-plane to the next bottle location. At block 408, the method 400 includes moving the probe just above the bottle level (e.g., the top of the bottle). At block 410, the method 400 includes measuring the ambient pressure in the probe with a pressure sensor to establish a threshold pressure level. At block 412, the method 400 includes vibrating the pill tray (e.g., via a vibration motor). At block 414, the method 400 includes turning on a vacuum pump to create a vacuum pressure within the retrieval probe. The vacuum pressure may be adjusted for pill size and shape. At block 416, the method 400 includes lowering the probe into the bottle at a reduced speed. At block 418, the method 400 includes stopping probe movement when the pill is captured by suction cup at the end of the probe. This may be determined based on a vacuum reading dropping below the threshold pressure level and/or via an activation of a probe limit switch. At block 420, the method 400 includes elevating the probe and confirming the pressure level is under the threshold pressure level for the sensor for a successful individual pill pick. At block 422, the method 400 includes, (a) if a determination is made that no pill was picked up successfully, returning to block 408, and (b) if a determination is made that a pill was picked up successfully, moving to block 424.

At block 424, the method 400 includes moving the probe to a z-axis origin (e.g., in an upward direction). At block 426, the method 400 includes moving the gantry in the xy-plane to the next available pre-dispensing tray slot. At block 428, the method 400 includes lowering the probe to a pre-dispensing height. At block 430, the method 400 includes releasing the pill by turning off the vacuum pump and opening a solenoid to clear the vacuum line. At block 432, the method 400 includes (a) if a determination is made that more than one pill was dispensed, moving to step 434 which includes (i) capturing the extra pill from the pre-dispensing tray and returning the extra pill to the corresponding bottle, and (ii) checking the pre-dispensing tray weight to confirm that the pre-dispensing tray includes the correct number of pills, and (b) if a determination is made that only one pill was dispensed, moving to block 436.

At block 436, the method 400 includes moving the probe to the z-axis origin (e.g., in an upward direction). At block 438, the method 400 includes confirming if more pills are being dispensed in this dispensing session. At block 440, the method 400 includes (a) if a determination is made that the pill picking is not complete, returning to block 406, and (b) if a determination is made that the pill picking is complete, moving to block 442. At block 442, the method 400 includes moving the gantry in the xy-plane to a park position and then moving the tray cover down. At block 444, the method 400 includes showing an alert for dose ready. At block 446, the method 400 includes turning the pre-dispensing tray to dispense medication when a button is pressed or other user input is detected. For example, the user input may comprise a fingerprint scan on the button, or a code that is entered on the user interface, or using a mobile application use code and/or face-identification, or a separate fingerprint scanner to verify and authenticate user for medication to be dispensed, or the user input can based on an external camera to unlock the system with face-identification or other user specific characteristic. Other user inputs prior to dispensing the solid dosage medicament are possible as well.

Figure 9:
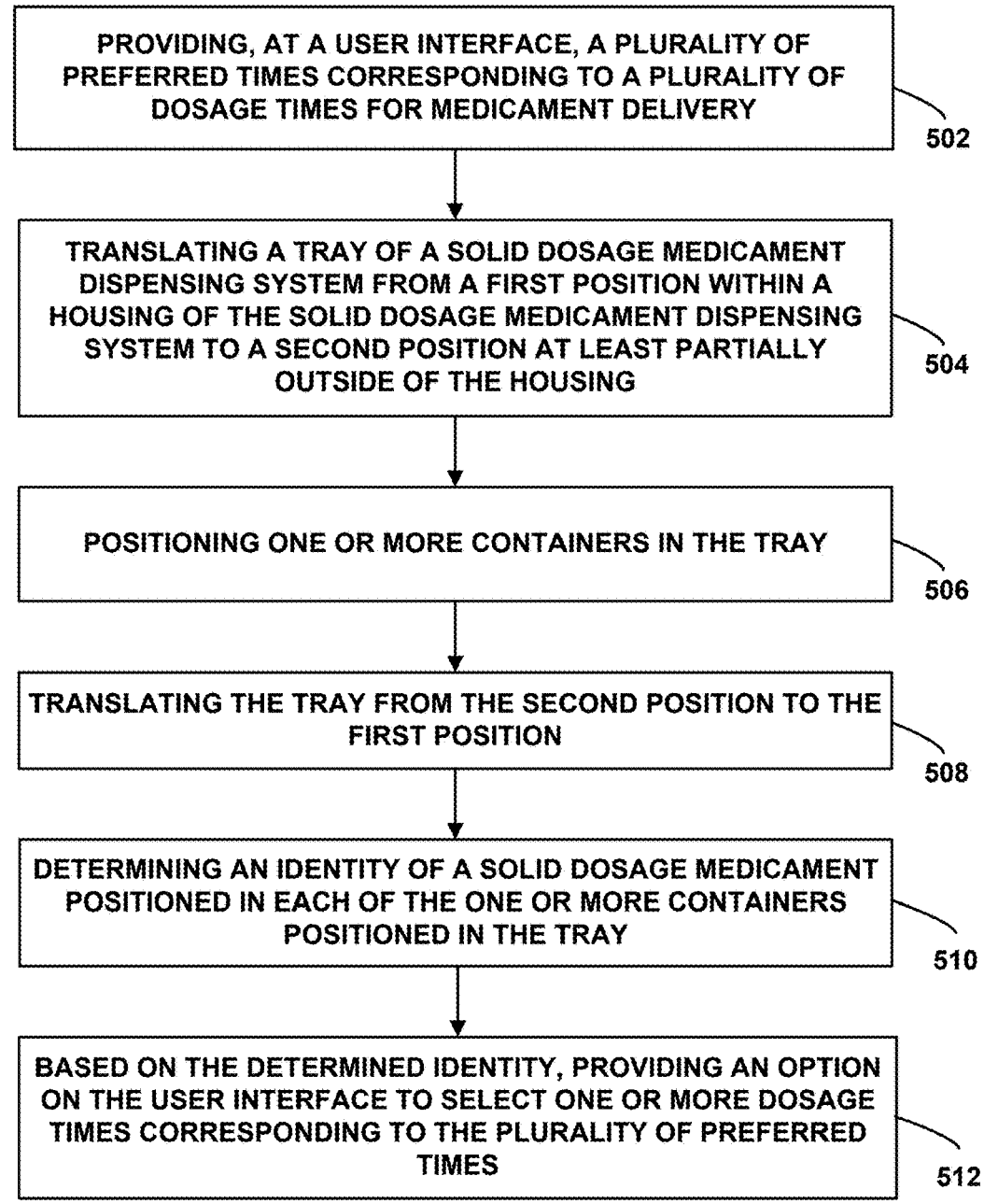
FIG. 9 is a flowchart of another example method, according to an example embodiment.

FIG. 9 is a block diagram of an example of a method 500. Method 500 shown in FIG. 9 presents an embodiment of a method that could be used with any of the systems or devices described above in relation to FIGS. 1-6C, as an example. Method 500 includes one or more operations, functions, and/or actions as illustrated by one or more of blocks 502-512. Although the blocks are illustrated in a sequential order, these blocks may also be performed in parallel, and/or in a different order than those described herein. Also, the various blocks may be combined into fewer blocks, divided into additional blocks, and/or removed based upon the desired implementation.

Initially, at block 502, the method 500 includes providing, at a user interface, a plurality of preferred times corresponding to a plurality of dosage times for medicament delivery. At block 504, the method 500 includes translating a tray of a solid dosage medicament dispensing system from a first position within a housing of the solid dosage medicament dispensing system to a second position at least partially outside of the housing. At block 506, the method 500 includes positioning one or more containers in the tray. At block 508, the method 500 includes translating the tray from the second position to the first position. At block 510, the method 500 includes determining an identity of a solid dosage medicament positioned in each of the one or more containers positioned in the tray. At block 512, the method 500 includes, based on the determined identity, providing an option on the user interface to select one or more dosage times corresponding to the plurality of preferred times.

In one example, the method 500 further includes, (a) based on the selected one or more dosage times, providing the solid dosage medicament to a pre-dispensing tray of the solid dosage medicament dispensing system, (b) if a user input is received at the user interface, dispensing the solid dosage medicament to an exterior of the housing, and (c) if no user input is received at the user interface within a threshold time period, returning the solid dosage medicament to the container.

Figure 10C:
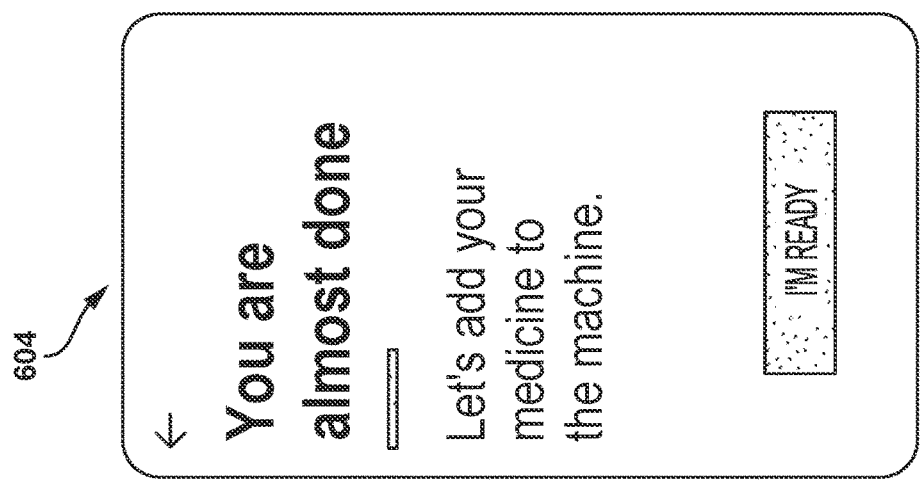
Figure 10B:
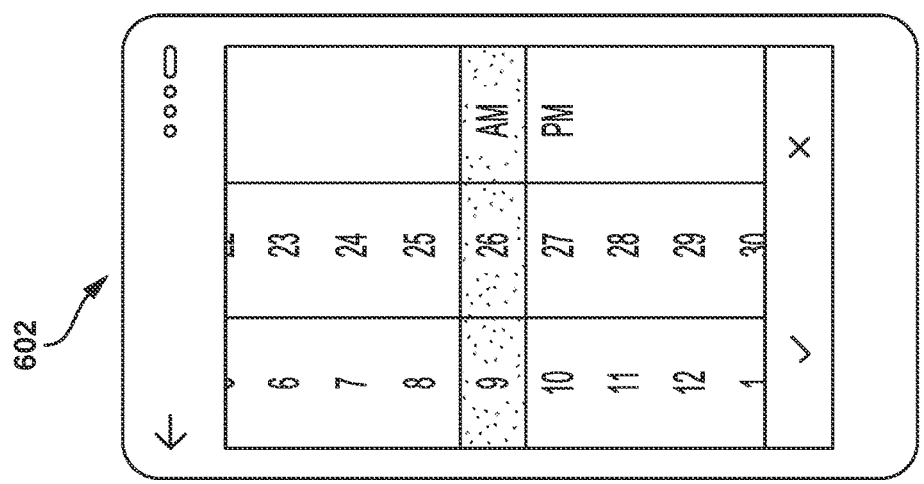
Figure 10A:
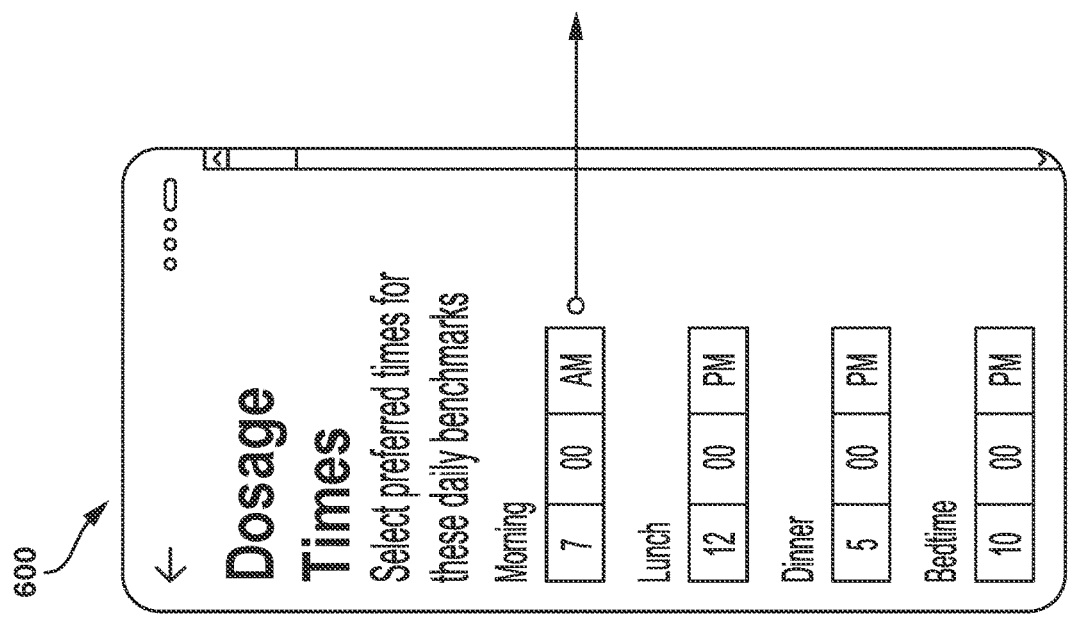
Figure 10F:
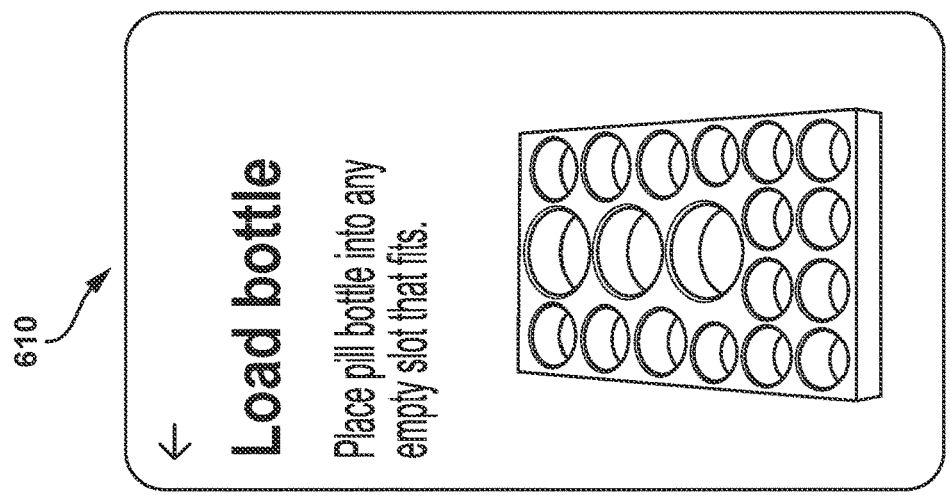
Figure 10E:
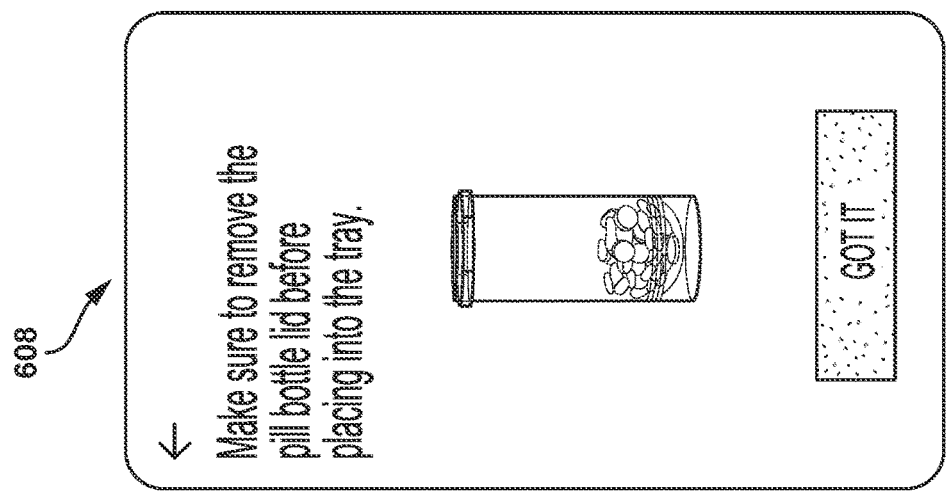
Figure 10D:
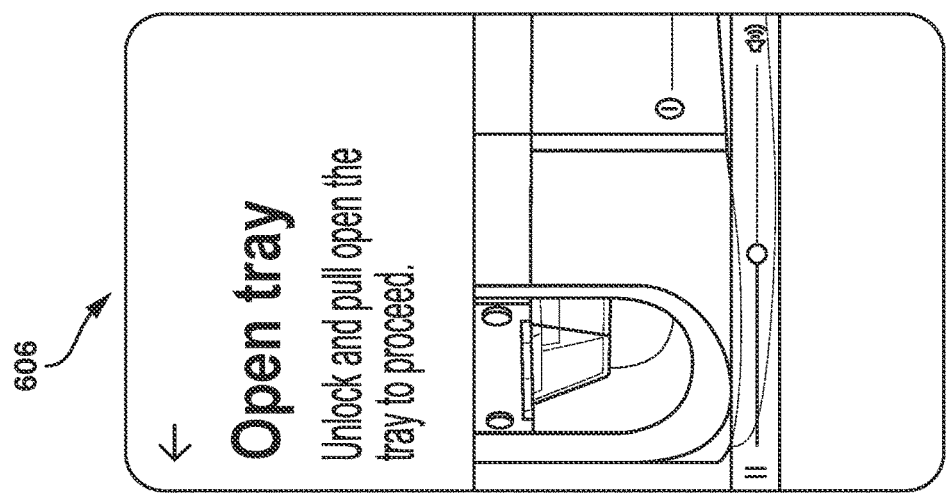
Figure 10G:
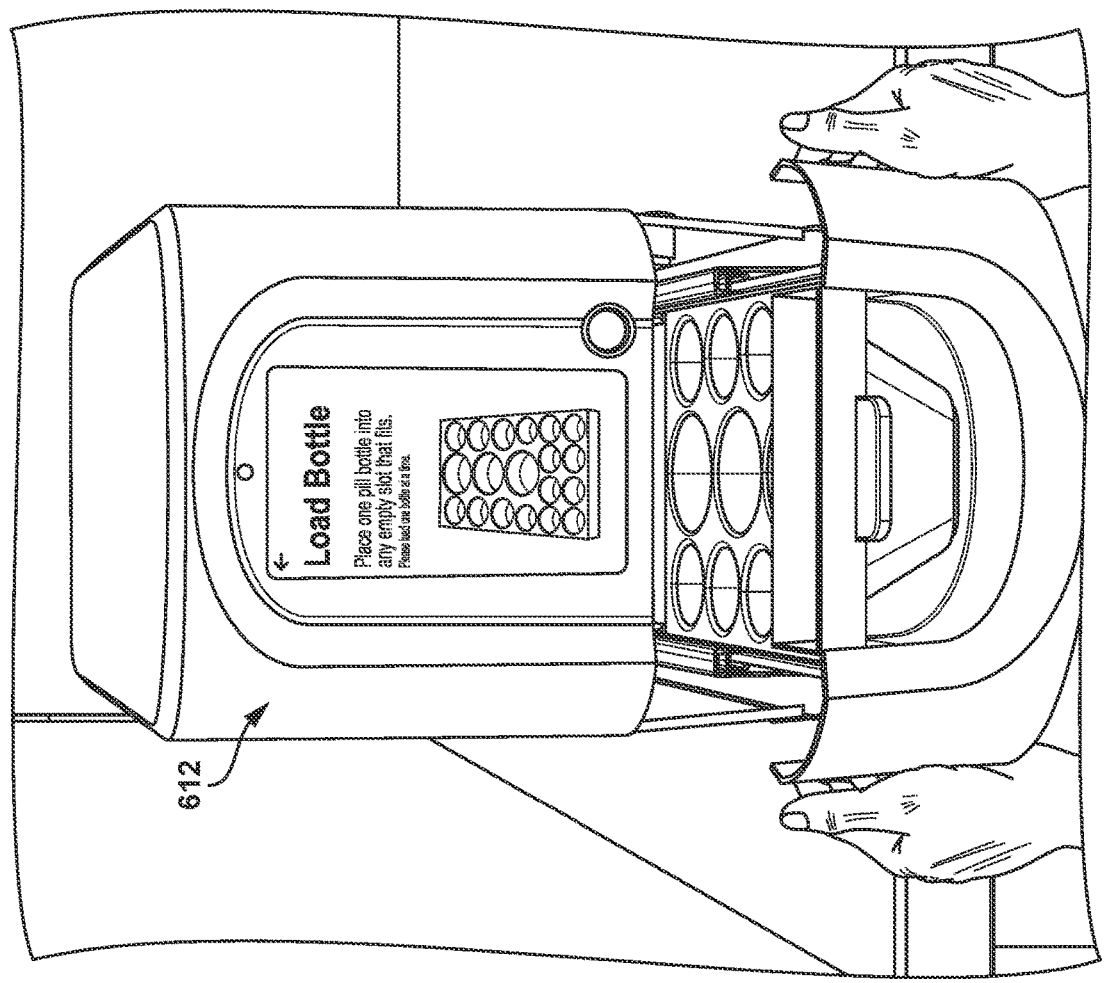

FIGS. 10A-10M illustrate various user interfaces of the solid dosage medicament dispensing system described above. In particular, FIGS. 10A-10M show user interfaces illustrating of one or more of the methods described above. FIG. 10A illustrates a user interface 600 in which a user can selected preferred times for daily benchmarks corresponding to times for the user to receive their medication. FIG. 10B illustrates a user interface 602 in which the user has selected the preferred time for a morning dosage. FIG. 10C illustrates a user interface 604 in which the user can add medication in pill bottles to the solid dosage medicament dispensing system. FIG. 10D illustrates a user interface 606 that instructs the user to unlock and pull open the tray. FIG. 10E illustrates a user interface 608 that instructs the user to move the pill bottle lid. FIG. 10F illustrates a user interface 610 that instructs the user to place the pill bottle into any empty slot in the tray. FIG. 10G is a graphical representation 612 of the solid dosage medicament dispensing system in a functional context of illustrating the user interface 610 of FIG. 10F.

Figure 10J:
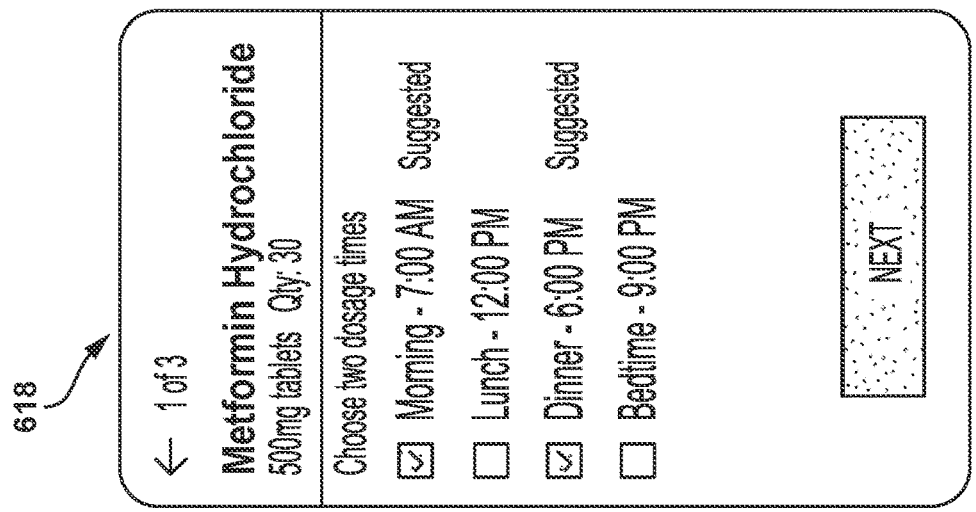
Figure 10I:
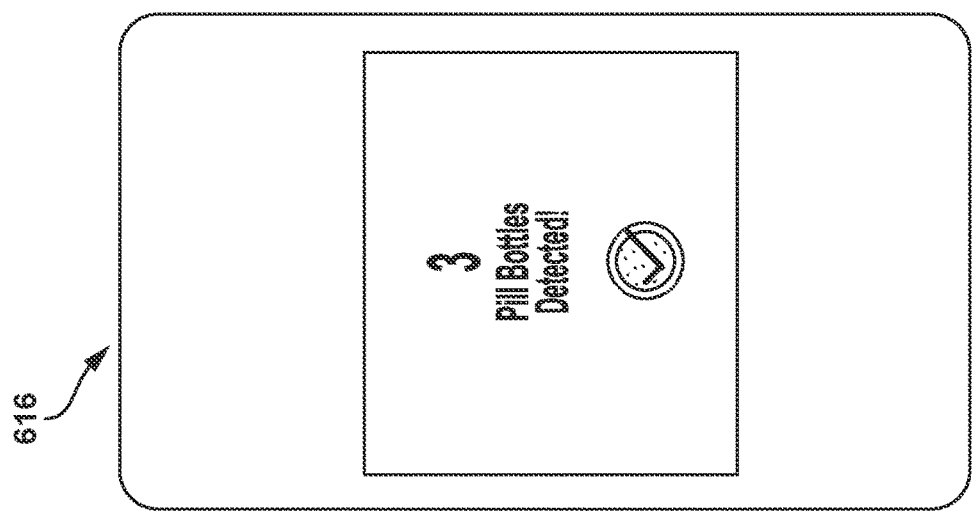
Figure 10H:
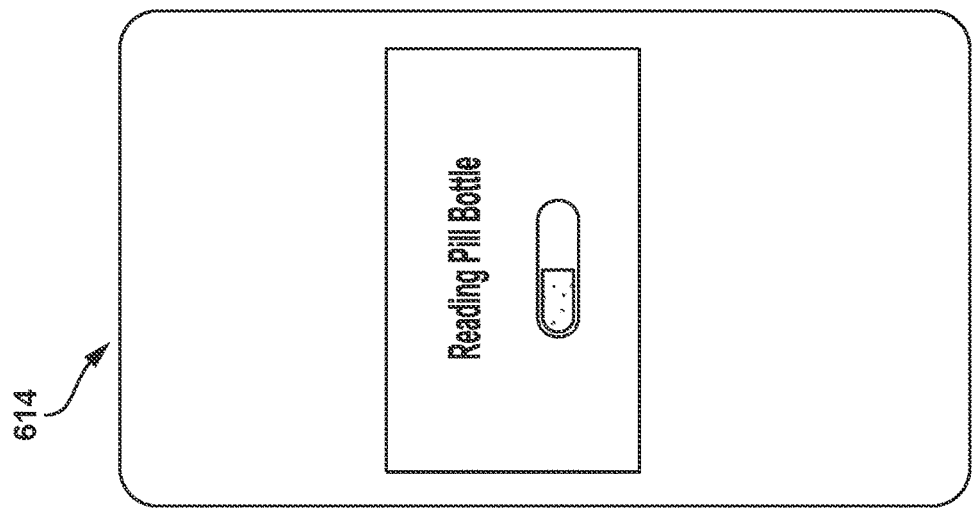

FIG. 10H illustrates a user interface 614 indicating that the solid dosage medicament dispensing system is reading the pill bottle that was just inserted into the tray. FIG. 10I illustrates a user interface 616 indicating that three pill bottles were detected by the solid dosage medicament dispensing system. FIG. 10J illustrates a user interface 618 displaying a first medicament detected in one of the three pill bottles, including an indication to select two dosage times from previously selected preferred dosage times. FIG. 10K illustrates a user interface 620 displaying a second medicament detected in one of the three pill bottles, including an indication to select two dosage times from previously selected preferred dosage times. FIG. 10L illustrates a user interface 622 displaying a third medicament detected in one of the three pill bottles, including an indication to select two dosage times from the previously selected preferred dosage times. FIG. 10M illustrates a user interface 624 providing a visual indication that the medicament has been successfully added to the solid dosage medicament dispensing system.

The methods described herein can be utilized effectively with any of the examples or variations of the devices and systems described above, as well as with other examples and variations not described explicitly in this document. The features of any of the systems, devices, or components thereof described in any of the examples herein can be used in any other suitable example of a device or device component.

It should be understood that arrangements described herein are for purposes of example only. As such, those skilled in the art will appreciate that other arrangements and other elements (e.g. machines, interfaces, functions, orders, and groupings of functions, etc.) can be used instead, and some elements may be omitted altogether according to the desired results. Further, many of the elements that are described are functional entities that may be implemented as discrete or distributed components or in conjunction with other components, in any suitable combination and location, or other structural elements described as independent structures may be combined.

While various aspects and examples have been disclosed herein, other aspects and examples will be apparent to those skilled in the art. The various aspects and examples disclosed herein are for purposes of illustration and are not intended to be limiting, with the true scope being indicated by the following claims, along with the full scope of equivalents to which such claims are entitled. It is also to be understood that the terminology used herein is for the purpose of describing particular examples only, and is not intended to be limiting.

What is claimed is:

1. A solid dosage medicament dispensing system, comprising:
    a housing;
    a tray and a tray cover coupled to the housing, wherein the tray cover is removably positioned within the housing over the tray which is configured to receive one or more containers, the tray cover comprising two panels arranged to pivot to opposite sides of the housing in an open position, and wherein the tray is configured to translate between a first position that is fixed relative to the housing and to a second position in which the tray is positioned at least partially outside of the housing to receive the one or more containers;
    a track enclosed in the housing;
    a gantry carrying a retrieval probe positioned on the track, wherein movement of the gantry relative to the track positions the retrieval probe along an x-y plane, and wherein the retrieval probe is moveable between the one or more containers when the tray is in the first position and fixed relative to the housing;

a pre-dispending tray, wherein the pre-dispensing tray is a rectangular tray comprising a plurality of compartments coupled within the housing adjacent to the tray in the first position;

a dispensing tray removably coupled to the housing below the pre-dispensing tray, wherein the dispensing tray is configured to receive a solid dosage medicament from the pre-dispensing tray when the dispensing tray is positioned within the housing;

a load cell positioned under the pre-dispensing tray, wherein the load cell is configured to weigh the contents of the pre-dispensing tray;

a user interface configured to receive one or more inputs from a user; and a control system configured to perform one or more functions of the solid dosage medicament dispensing system based on the one or more inputs received from the user.

2. The solid dosage medicament dispensing system of claim 1, wherein each container of the one or more containers includes a solid dosage medicament.

3. The solid dosage medicament dispensing system of claim 1, further comprising:

a vacuum pump in communication with the retrieval probe and configured to create a negative pressure within the retrieval probe.

4. The dosage medicament dispensing system of claim 1, wherein the control system is configured to:

determine an identity of a solid dosage medicament positioned in a container of the one or more containers positioned in the tray; and provide an option on the user interface to select a dosage time based on the determined identity.

5. The dosage medicament dispensing system of claim 3, wherein the control system is configured to:

vibrate the tray;

position, by the gantry, the retrieval probe at a location above a container of the one or more containers positioned in the tray;

lower the retrieval probe into the container to capture a solid dosage medicament from the container; and determine, based on the negative pressure, whether the retrieval probe has captured the solid dosage medicament.

6. The dosage medicament dispensing system of claim 5, wherein the control system is configured to:

in response to a determination that the retrieval probe has not captured the solid dosage medicament, direct the gantry to adjust a lateral position of the retrieval probe.

7. The dosage medicament dispensing system of claim 6, wherein adjusting the lateral position of the retrieval probe via the gantry comprises initially lowering the retrieval probe into a first position in the container and moving the retrieval probe via the gantry along a spiral path relative to the first position until a determination, based on the negative pressure, is made that the retrieval probe has captured the solid dosage medicament.

8. The dosage medicament dispensing system of claim 7, wherein the first position is in the middle of the container.

9. The dosage medicament dispensing system of claim 5, wherein the control system is further configured to:

move the retrieval probe to the pre-dispensing tray in response to a determination that the retrieval probe has captured the solid dosage medicament; and release the solid dosage medicament from the retrieval probe into the pre-dispensing tray.

10. The dosage medicament dispensing system of claim 9, wherein the control system is further configured to:

if a user input is received at the user interface, dispense the solid dosage medicament to an exterior of the housing; and if no user input is received at the user interface within a threshold time period, (i) move the retrieval probe to the pre-dispensing tray, (ii) capture the solid dosage medicament from the pre-dispensing tray, and (iii) return the solid dosage medicament to the container.

11. The dosage medicament dispensing system of claim 5, wherein determining whether the retrieval probe has captured the solid dosage medicament comprises:

comparing a detected vacuum reading of the retrieval probe to a threshold level;

if the detected vacuum reading is less than the threshold level, determining that the retrieval probe has captured the solid dosage medicament; and if the detected vacuum reading is not less than the threshold level, determining that the retrieval probe has not captured the solid dosage medicament.

* * * * *